United States Patent [19]

Southgate et al.

[11] 4,349,880

[45] Sep. 14, 1982

[54] INSPECTION SYSTEM FOR DETECTING DEFECTS IN REGULAR PATTERNS

[75] Inventors: Peter D. Southgate, Princeton; John P. Beltz, Willingboro, both of N.J.

[73] Assignee: RCA Corporation, New York, N.Y.

[21] Appl. No.: 164,348

[22] Filed: Jun. 30, 1980

Related U.S. Application Data

[63] Continuation-in-part of Ser. No. 21,826, Mar. 19, 1979, abandoned.

[51] Int. Cl.³ .................. G06F 15/20; G06F 15/336
[52] U.S. Cl. ................................. 364/507; 250/563; 340/146.3 Q; 356/237; 358/106; 364/819
[58] Field of Search ............. 364/507, 515, 573, 728, 364/819; 340/146.3 F, 146.3 G, 146.3 Q; 358/101, 106; 250/562, 563, 571, 572; 356/237, 239

[56] References Cited
U.S. PATENT DOCUMENTS

| | | | |
|---|---|---|---|
| 3,614,232 | 10/1971 | Mathisen | 356/237 X |
| 3,658,420 | 4/1972 | Axelrod | 356/237 X |
| 3,738,752 | 6/1973 | Heinz et al. | 356/239 X |
| 3,882,461 | 5/1975 | Vinnemann et al. | 340/146.3 ED |
| 3,887,762 | 6/1975 | Uno et al. | 358/106 |
| 3,958,127 | 5/1976 | Faulhaber et al. | 250/563 |
| 3,963,354 | 6/1976 | Feldman et al. | 250/562 X |
| 3,972,616 | 8/1976 | Minami et al. | 356/239 X |
| 3,982,426 | 9/1976 | Newhouse et al. | 364/507 X |
| 4,005,281 | 1/1977 | Faulhaber et al. | 364/507 |
| 4,149,120 | 4/1979 | Richter | 364/573 X |

Primary Examiner—Jerry Smith
Attorney, Agent, or Firm—Eugene M. Whitacre; Glenn H. Bruestle; Dennis H. Irlbeck

[57] ABSTRACT

The inspection system detects defects in regular patterns wherein the elements of the patterns may have variations in period. In the system a camera, having a photoelectric sensor therein, is mechanically moved to permit the sensor to scan and detect the elements of a pattern. The system includes circuitry for processing the output of the sensor. The circuitry includes portions for quantizing the sensor output signal, for storing the quantized signal of a portion of a scan, for determining element period from the quanitized signal and for controlling the output of the storage portion at times related to element period. The circuitry also includes portions for correlating the output from the storing portion with a real time quantized signal of the same scan and for indicating the presence of an error related to a pattern defect in response to a miscorrelation signal from the correlating portion.

10 Claims, 27 Drawing Figures

DEVICES: A BUFFER AMPLIFIERS
B D-TYPE FLIP-FLOP
C AND GATE
D ANALOG GATE
E DIFFERENTIAL AMPLIFIER

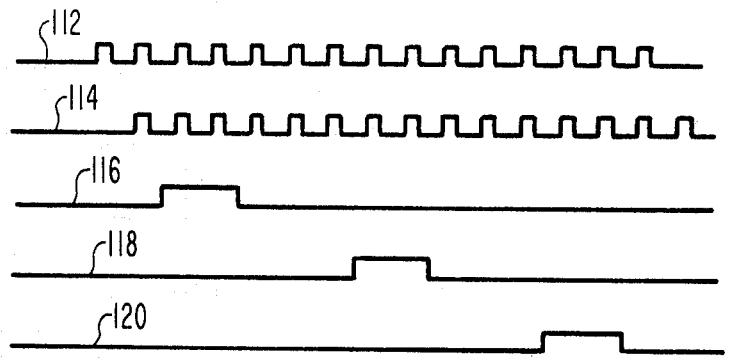
Fig.8
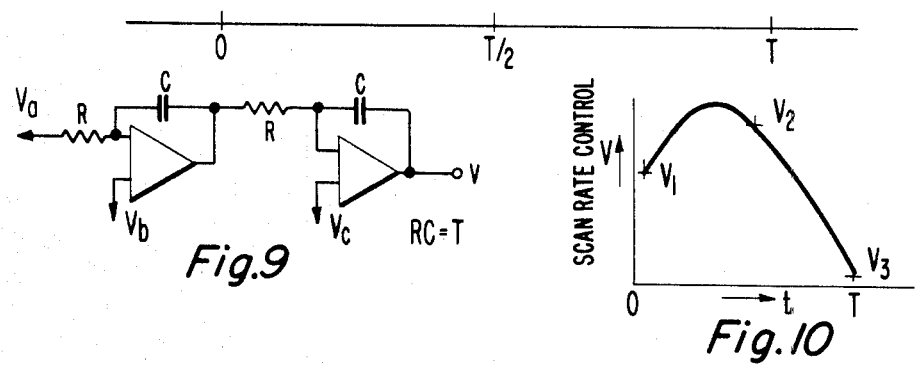
Fig.9
Fig.10
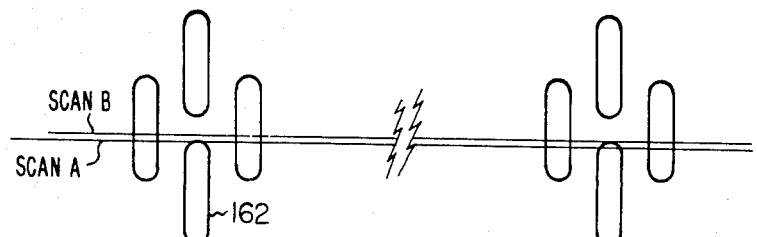
Fig.12
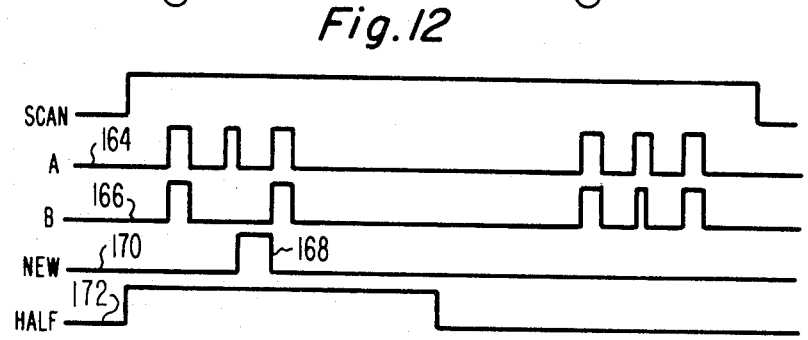
Fig.13

| CLEAR \ OPAQUE | 1/2  2/4 | 1/2  3/5 | 1  2/4 | 1  3/5 |
|---|---|---|---|---|
| 1/2  2/4 | 0 | 2 | 8 | A |
| 1/2  3/4 | 1 | 3 | 9 | B |
| 1  2/4 | 4 | 6 | C | E |
| 1  3/4 | 5 | 7 | D | F |

| INPUTS | | | | | | | | OUTPUT | | |
|---|---|---|---|---|---|---|---|---|---|---|
| $A_3$ | $C_1$ | $B_2$ | $A_2$ | $B_1$ | $A_1$ | | | $S_4$ | | |
| 1 | 0 | 0 | 0 | 0 | 0 | | | 0 | | |
| 1 | 0 | 0 | 0 | 0 | 1 | | | 0 | | |
| 1 | 0 | 0 | 0 | 1 | 0 | | | 0 | | |
| 1 | 0 | 0 | 0 | 1 | 1 | | | 0 | | |
| 1 | 0 | 0 | 1 | 0 | 0 | | | 0 | | |
| 1 | 0 | 0 | 1 | 0 | 1 | | | 0 | | |
| 1 | 0 | 0 | 1 | 1 | 0 | | | 0 | | |
| 1 | 0 | 0 | 1 | 1 | 1 | | | 1 | | |
| 1 | 0 | 1 | 0 | 0 | 0 | | | 0 | | |
| 1 | 0 | 1 | 0 | 0 | 1 | | | 0 | | |
| 1 | 0 | 1 | 0 | 1 | 0 | | | 0 | | |
| 1 | 0 | 1 | 0 | 1 | 1 | | | 1 | | |
| 0 | 0 | 1 | 1 | 0 | 0 | | | 0 | | |
| 1 | 0 | 1 | 1 | 0 | 1 | | | 1 | | |
| 1 | 0 | 1 | 1 | 1 | 0 | | | 1 | | |
| 1 | 0 | 1 | 1 | 1 | 1 | | | 1 | | |
| 1 | 1 | 0 | 0 | 0 | 0 | | | 0 | | |
| 1 | 1 | 0 | 0 | 0 | 1 | | | 0 | | |
| 1 | 1 | 0 | 0 | 1 | 0 | | | 0 | | |
| 1 | 1 | 0 | 0 | 1 | 1 | | | 0 | | |
| 1 | 1 | 0 | 1 | 0 | 0 | | | 0 | | |
| 1 | 1 | 0 | 1 | 0 | 1 | | | 1 | | |
| 1 | 1 | 0 | 1 | 1 | 0 | | | 1 | | |
| 1 | 1 | 0 | 1 | 1 | 1 | | | 1 | | |
| 1 | 1 | 1 | 0 | 0 | 0 | | | 0 | | |
| 1 | 1 | 1 | 0 | 0 | 1 | | | 1 | | |
| 1 | 1 | 1 | 0 | 1 | 0 | | | 1 | | |
| 1 | 1 | 1 | 0 | 1 | 1 | | | 1 | | |
| 1 | 1 | 1 | 1 | 0 | 0 | | | 1 | | |
| 1 | 1 | 1 | 1 | 0 | 1 | | | 1 | | |
| 1 | 1 | 1 | 1 | 1 | 0 | | | 1 | | |
| 1 | 1 | 1 | 1 | 1 | 1 | | | 1 | | |

MAJORITY GATE TRUTH TABLE

*Fig. 27*

INSPECTION SYSTEM FOR DETECTING DEFECTS IN REGULAR PATTERNS

This is a continuation-in-part of application Ser. No. 021,826, filed Mar. 19, 1979 and now abandoned.

BACKGROUND OF THE INVENTION

This invention relates to the detection of defects in regular periodic patterns and particularly to an inspection system for detecting defects in such patterns wherein the elements of the patterns have variable periodicity. Although the present invention may be utilized to detect defects in many different types of regular periodic patterns, it hereinafter will be described with respect to the detection of defects in photographic master plates used in forming shadow masks of color television picture tubes.

Shadow masks used in color picture tubes are manufactured by a photolithography method in which a glass working plate with a suitable pattern on it is pressed against a photoresist coated steel sheet while the photoresist material is exposed by a suitable light source. During the many repetitions of this procedure, the pattern on the glass plate can become damaged. Either small portions of the black dots or bars which form the pattern can become torn off, or dirt particles can become pressed into the pattern. Masks made from defective plates will be faulty and must be discarded. Therefore, there is a need to periodically inspect the glass working plates.

Small defects of the dark dots or bars superimposed on a light background are very difficult to see when the pattern is viewed without magnification. This is in marked contrast to the negative pattern, such as is formed by the finished shadow mask, where enlarged or extra holes are quite visible, particularly to a trained observer. One way of enhancing visibility of some defects in a working plate is to superimpose a closely matched negative plate. Missing parts of the pattern will then show up as bright transmission spots. If the negative is shifted, extra dark spots can be given an enhanced visibility. However, this technique has a limited usefulness. For a satisfactory complete inspection, up to now it has been necessary to visually scan the plate under magnification, a process taking about 2 hours per plate.

A problem involved in automating the inspection of regular periodic patterns occurs when the pattern periodicity that is the element-to-element spacing of the pattern, varies over the pattern. The present invention solves this problem while providing an essentially automatic inspection system.

SUMMARY OF THE INVENTION

An inspection system is provided which detects defects in regular patterns wherein the elements of the patterns have variations in period. The system includes means for scanning and detecting the elements of a pattern and means for processing an output signal from the scanning and detecting means during scanning. The means for processing includes means for quantizing the output signal from the scanning and detecting means into binary digital signals, main storage means for storing the quantized signal of a portion of a scan, means for determining element period from the quantized signal and for controlling the output of the main storage means at times related to element period, means for correlating the output from the main storing means with a real time quantized signal of the same scan, and means for indicating the presence of an error related to a pattern defect in response to a miscorrelation signal from the correlating means.

BRIEF DESCRIPTION OF THE DRAWINGS

FIG. 8 is a schematic diagram showing a series of waveforms for linearizing a video signal varying in a quadradic manner.

FIG. 9 is a circuit diagram for producing a quadradic output.

FIG. 10 is a graph showing the scan rate control signal for providing quadradic correction.

FIG. 12 is a schematic diagram showing scan lines on portions of a pattern.

FIG. 13 is a schematic diagram showing a series of waveforms produced by the circuit of FIG. 11 during the scans shown in FIG. 12.

FIG. 27 is a truth table for various conditions into the majority gate of the correlation algorithm circuit of FIGS. 25 and 26.

DETAILED DESCRIPTION

Figure 4:
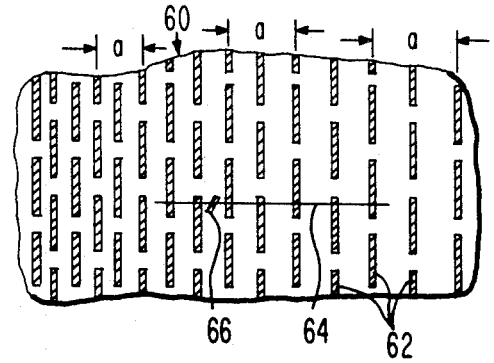
FIG. 4 is a partial view of a pattern on a working plate.

The present inspection system is used for scanning a regular periodic pattern, such as a negative aperture pattern on a glass working plate used for exposing photoresist material on a metal sheet in the construction of shadow masks for color television picture tubes. One such aperture pattern is shown in FIG. 4 wherein the period is the horizontal element-to-element spacing. Scanning of a pattern takes two forms. The first is the gross mechanical scanning of a video sensor in a specific manner over the pattern while the second is the electrical scanning of a line array target within the video sensor. The purpose of scanning patterns is to determine and locate defects in the patterns. The defects are discovered by a portion of the inspection system which autocorrelates the sensor output, also called the video signal, with itself. Autocorrelation in one form of the invention is accomplished by providing a delay in the video signal and then comparing the signals by a method such as subtraction of the delayed video signal from the original video signal. Any signal remaining after this procedure is an error signal indicating the presence of a defect. This autocorrelating technique will provide a meaningful result when the periodicity of the pattern is uniform. However, when the pattern periodicity is nonuniform, such as in the pattern of FIG. 4, the present invention provides means for compensating for the nonuniformity so that autocorrelation may be performed.

The present inspection system, which may be implemented in either an analog form or in a digital form, handles the problem of autocorrelating a video signal when the periodicity in elements of a pattern is nonuniform. In the analog system, the video signal is delayed a set time which is related to the anticipated pattern period and a difference signal is obtained by comparing the original video signal with the delayed video signal. The difference signal is then used to control video sensor scan rate so that the period of the video signal output from the video sensor matches the period of the delayed video signal. In the digital system, scan rate is held constant and the time of computer storage of the delayed video signal is varied in order to match periodicity of the original and delayed signals.

Figure 1:
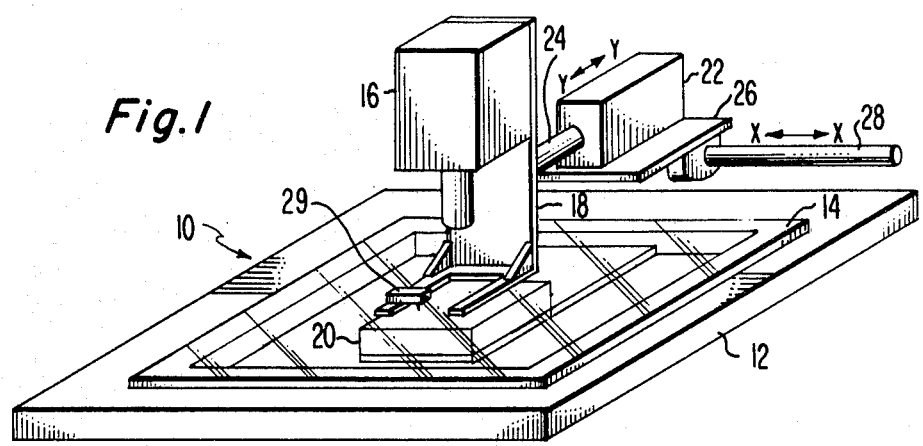
FIG. 1 is a perspective view of a video sensor scan apparatus including a glass working plate on a base.

The components and functions of each type of inspection system will now be discussed in greater detail. First, the analog system is presented and then the digital system. One embodiment of a mechanical scanning apparatus 10 of the present inspection system is shown in FIG. 1. The apparatus 10 includes a base 12 on which a glass working plate 14, having a regular pattern thereon, is mounted. The base 12 supports the edges of the plate 14 and is open in the center so as not to obstruct the photographic pattern on the plate 14. A video sensor 16, such as a solid state photodiode array, is mounted on a platform 18 directly above the working plate 14. A light box 20 is located underneath the plate 14 directly below the video sensor 16. The platform 18 is moveable in two directions, X—X and Y—Y. Movement of the sensor 16 in the Y—Y direction is by actuation of a suitable unit 22 such as a pneumatic cylinder or electrical selenoid, attached to the platform 18 by a shaft 24. The unit 22 sits on a second platform 26 which is moveable along a shaft 28 by another unit, not shown. A marking unit 29 also is shown attached to a portion of the platform 18 for indicating areas of defects on the working plate.

The video sensor 16 in the system may be a camera having a lens for collecting light passing through a pattern and for imaging the pattern onto a photoelectric sensor within the camera. The light is diffused to provide a wide range of incident light angles to reduce sensitivity to scratches. The sensor reads light transmitted through a glass plate on which an emulsion pattern is located. The image lens, such as a Vivitar 55 mm 2.8 Automacro lens, is housed in a light tight enclosure with a solid state line scanner such as a 1728 element photodiode array, commercially available from the Reticon Corporation. The magnification of the lens is 1.5. Each scanner element is 15 $\mu$m wide which corresponds to 0.4 mils on the working plate pattern. The scanner elements integrate collected light, and when addressed, discharge the integrated signal. Each scanner element acts independently, so that output signal is a series of charge pulses. These pulses are processed in a sample and hold amplifier, and the resultant output of the camera is a boxcar video signal in which each level is representative of the amount of light collected by that element during one scan period.

Figure 2:
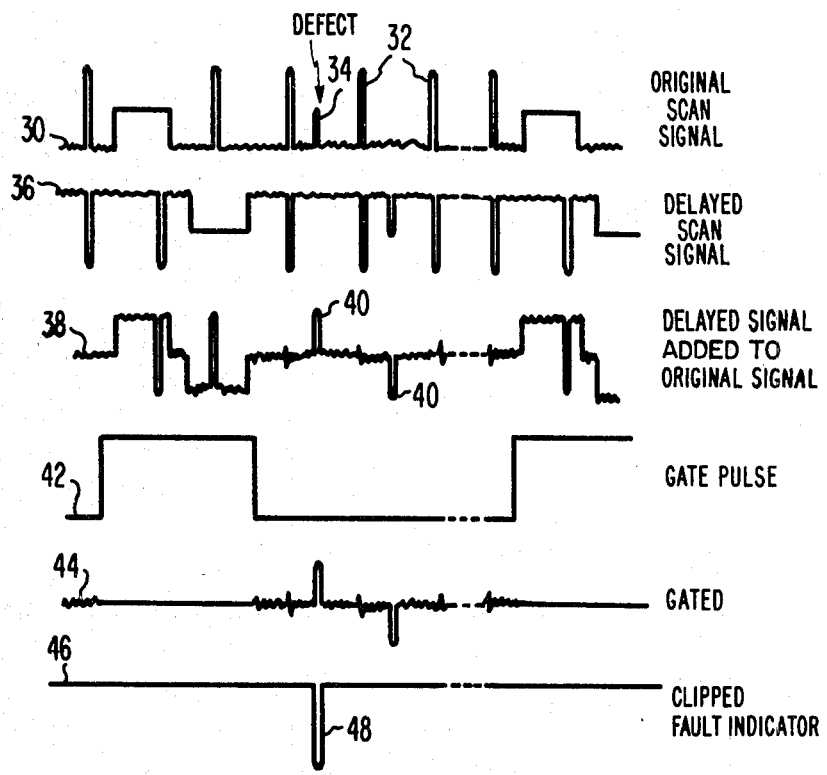
FIG. 2 is a schematic diagram showing a series of analog waveforms illustrating correlation of a video signal with itself.

The principle of autocorrelating the output signal from the video sensor 16 in an analog system is illustrated in the waveforms shown in FIG. 2. The upper waveform 30 is the video sensor output signal which consists of a series of parallel narrow bright bars 32 indicating elements of the pattern being scanned by the video sensor. An extra pulse 34 is present because of a defect in the pattern. The second waveform 36 shows the original waveform 30 inverted and delayed one period. The second waveform 36 is next added to the first waveform 30 to obtain a third waveform 38. The defect signal 40 appears prominently in both polarities in the third waveform 38. Also shown in the third waveform 38 is some noise and extra small spikes which can appear if the delay time varies slightly from one exact period. The fourth waveform 42 is a gating waveform for selecting those portions of the third subtracted waveform 38 during which a pertinent portion of the video signal occurs in both the original and delayed waveforms, 30 and 36, respectively. The fifth waveform 44 shows a portion of the third subtracted waveform 38 passed by the fourth gating waveform 42. Finally, the sixth waveform 46 shows the gated signal clipped at a suitable threshold level thereby giving an unambiguous indication of defects of greater than a certain size, such as the spike 48.

Figure 3:
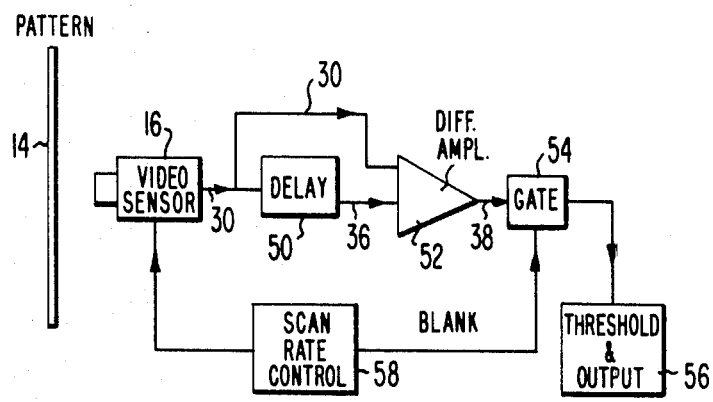
FIG. 3 is a block diagram of autocorrelation components in one embodiment of the present inspection system.

Analog circuits to achieve each of the foregoing functions are well known in the art. A block diagram of the interconnection of these circuits is shown in FIG. 3. The output 30 of the video sensor 16 is fed both to a suitable delay line 50 such as an acoustic glass line or a solid state CCD device and to a differential amplifier 52. The output 36 of the delay line 50 is also fed into the differential amplifier 52. The output of the differential amplifier 52 is the subtracted waveform 38. This output 38 is fed into a gating circuit 54 which gates the subtracted waveform 38 to obtain the gated waveform 44. The gated waveform 44 is fed to the threshold and output circuit 56 where it is clipped and any defects remaining are indicated. The block diagram also includes a scan rate control unit 58 with inputs to both the camera 16 and gate circuit 54.

Although the foregoing autocorrelation example has been described with respect to a pattern of uniform periodicity, the periodicity of the pattern may vary across the scan distance. In such case, the video signal must be linearized before the correlation processing can be performed. The periodicity of the video signal may vary in a linear fashion requiring two variables to specify its form, or the periodicity may vary in a quadratic or higher order fashion requiring three or more variables. For each variable, an error signal is required, and for each error signal, the video signal must be sampled at an appropriate point along the scan.

Figure 5:
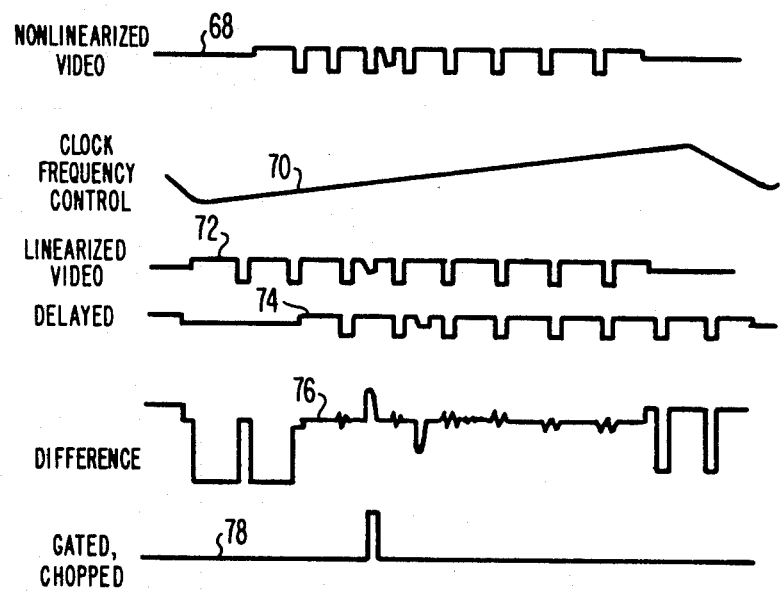
FIG. 5 is a schematic diagram showing a series of analog waveforms illustrating linearization of a linearly varying video signal.

FIG. 4 shows a portion of a pattern 60 having a linear variation in periodicity of elements 62 of the pattern. The period in the pattern 60 is labelled "a" and, as can be seen, varies horizontally across the pattern. The solid horizontal line 64 on the pattern 60 is the image formed on a solid state photodiode linear array which is read out by a clock of variable frequency. The small mark 66 on the pattern represents a defect. If the output rate of the photodiode linear array were not linearized, it would appear as the first waveform 68 in FIG. 5. However, the video sensor output can be linearized by appropriately changing the scan rate. The second waveform 70 of FIG. 5 shows a saw-tooth variation in clock frequency that is necessary to change the scan rate to obtain the linearized video signal 72 shown as the third waveform of FIG. 5. When this change in frequency is arranged to be proportionally higher as the wide-spaced pattern elements are read out, the video pattern period will remain substantially constant. Subsequent waveforms of FIG. 5 show the delayed video signal 74, the difference signal 76 and the gated chopped signal 78.

Figure 6:
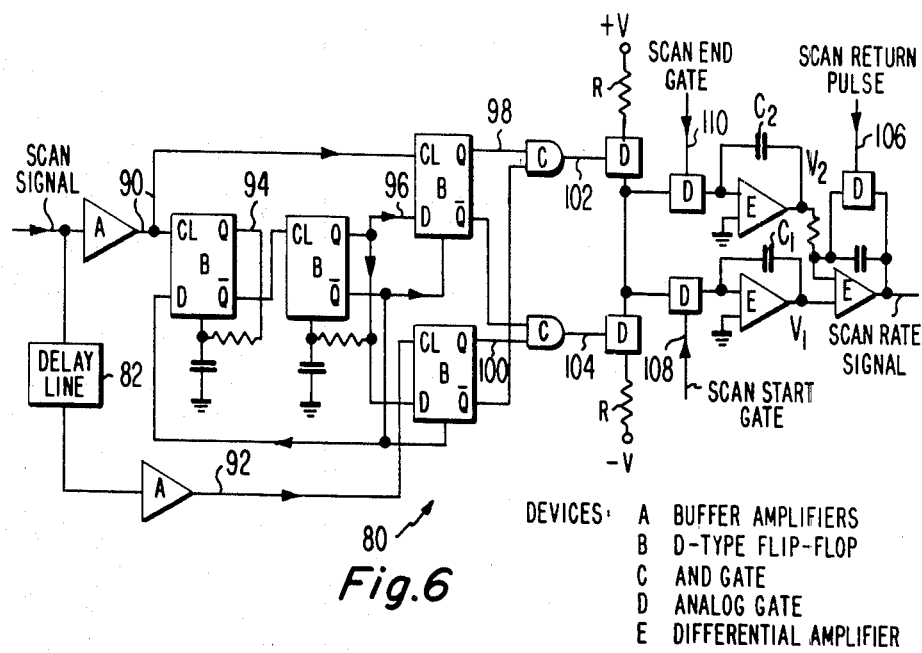
FIG. 6 is a circuit diagram of an analog linearization circuit.
Figure 7:
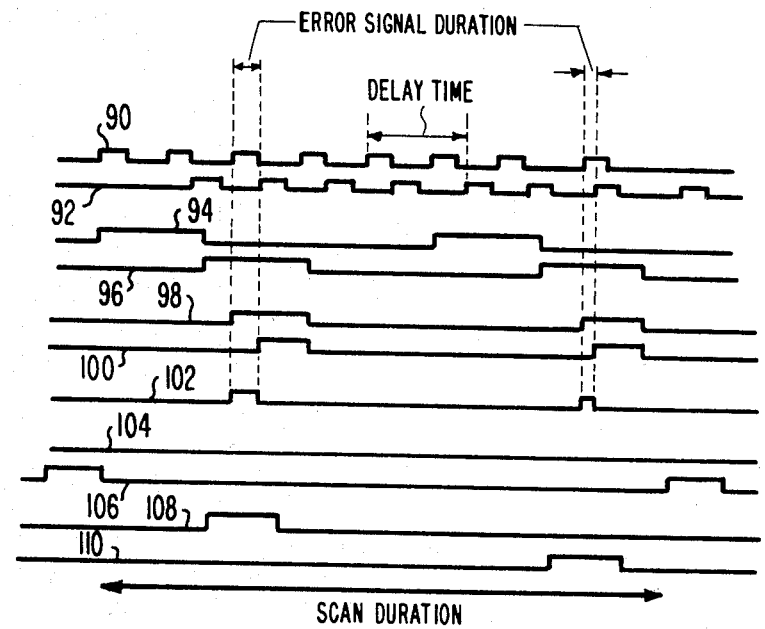
FIG. 7 is a schematic diagram showing a series of waveforms for obtaining a linearizing signal.

The appropriate saw-tooth waveform 70 of FIG. 5 can be generated by an analog circuit 80 shown in FIG. 6. This circuit 80 is an integrating circuit wherein the initial value and rate of rise of the output signal are determined by the voltages on the two capacitances $C_1$ and $C_2$. If the originally generated waveform does not give accurate linearization, the capacitor voltages are incremented by an error signal which drops to zero only when linearization has been achieved. The portion of the circuit 80 preceding the capacitors $C_1$ and $C_2$ has the function of generating these incrementing voltages. The functioning of the circuit 80 can be seen from the waveforms of FIG. 7. Essential to the operation of the circuit 80 is a delay line 82 which delays the video signal by a time equal to a desired period or a multiple thereof. The first waveform 90 in FIG. 7 shows the video signal as it comes from the scanning sensor. The second waveform 92 shows the video signal after it has been delayed a period greater than the desired period but less than twice the desired period. The video signal triggers a pulse generator having an output waveform 94 which in turn triggers a second pulse generator having an output waveform 96. The waveform 96 from the second pulse generator gives windows for selecting video pulses near the beginning and end of the scan. Waveforms 98 and 100 are then generated by the leading edges of the initial video and delayed video pulses which fall within the windows of the waveform 96. If the initial video leads the delayed video, the difference pulse is applied to a switch which charges the capacitor positive during the pulse period, while if the delayed video leads, the capacitor is charged negative. This difference pulse, appropriately signed, is the error signal 102 or 104 which corrects the clock frequency control. A further pair of switches are arranged to divert the error signal to $C_1$ or $C_2$ depending on whether the window is located at the start or finish of the scan. The remaining three waveforms in FIG. 7 are the scan return pulse 106, the scan start gate signal 108 and the scan end gate signal 110.

The foregoing described linearization circuit 80 will provide an appropriate correction for a linear variation in the spatial pattern periodicity. However, if the pattern variation has quadratic or higher components, more than two capacitors and voltages will be required to correct for the variation. These voltages will correspond to error signals taken at various points along the scan and are fed into a control waveform generating circuit containing several stages of integration. The error signals between a video signal 112 and a delayed video signal 114 from the start, middle and end of a scan are sampled by the windows in gating waveforms 116, 118 and 120 as shown in FIG. 8. These error signals are used to increment the control voltages $V_1$, $V_2$ and $V_3$. However, first these three voltages are converted into another set of three voltages, as follows, using amplifier-resistor networks well known in the art.

$$V_a = 2V_1 = 4V_2 + 3V_3$$

$$V_b = -2V_1 + 4V_2 - V_3$$

$$V_c = V_1$$

These voltages are then fed into the circuit of FIG. 9 which will give a quadratic output of the form, $$V = 2(V_1 - 2V_2 + V_3)(t/T)^2 + (-3V_1 + 4V_2 - V_3)(t/T) + V_1$$

where T is the scan time. This waveform has the property of passing through voltages $V_1$, $V_2$ and $V_3$ when $t/T = 0$, $\frac{1}{2}$ and 1 respectively, as shown in FIG. 10.

The embodiment described above shows only one way in which the present invention can be applied. In general, the video sensor which converts the pattern into a signal could be any of a variety of optical, electrical, mechanical or other detectors, scanned in any way which is controlled by a waveform determined by the stored control voltages. Similarly, the signal delay line may be made in a number of well established ways.

Figures 11, 14:
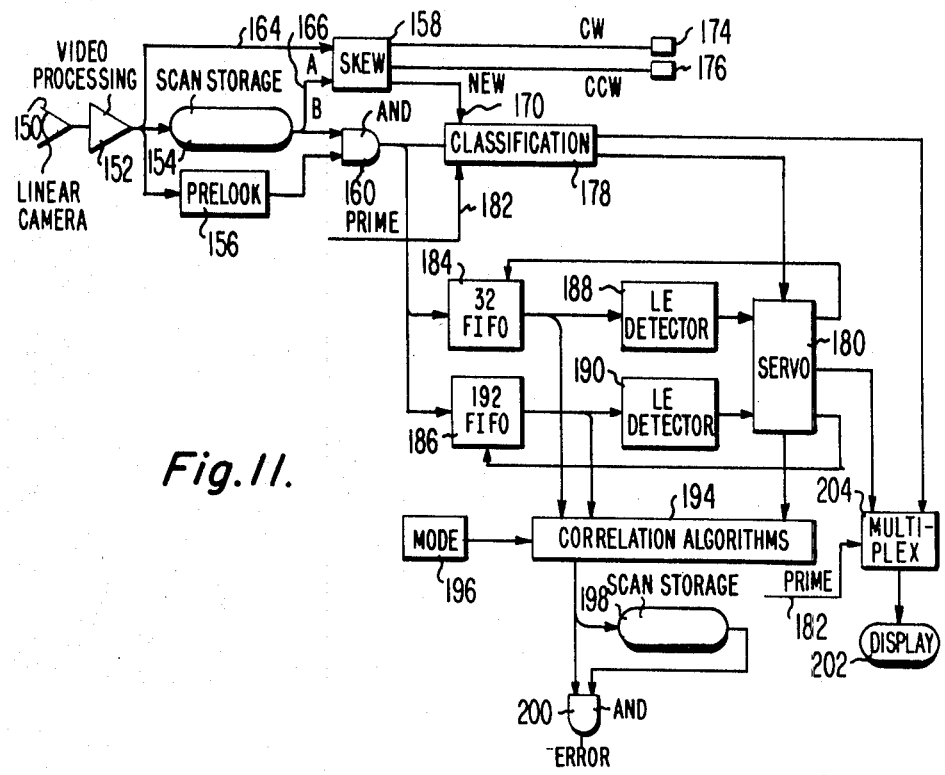
FIG. 11 is a circuit diagram of a digital inspection system.
FIG. 14 is a table showing the various optional settings for the mode unit of the circuit of FIG. 11.

A circuit incorporating a digital embodiment is shown in the block diagram of FIG. 11. In this embodiment, digital techniques are used exclusively after the video signal has been quantized, with the various logic modules locked into a crystal controlled clock. The digital system is fully adaptive to a wide range of patterns, with the only operator adjustment necessary being alignment of the photographic plate to a video sensor, such a camera, utilizing controlled indicators.

In the digital system, the video sensor scan rate is not linearized as in the analog system. Instead, the equivalent result is achieved by controlling the time of storage of the video signal so that the original and delayed video signals are in phase when fed into the correlation unit.

The output signal from a camera 150 is fed into video processing circuits 152. Three functions are performed in the video processing circuit 152. The first function is automatic gain control for maintaining a peak to peak video signal (e.g. 5 volts) over a range of inputs (e.g. from $\frac{1}{2}$ volt to 2 volts). Automatic gain control action compensates for aging of the lamp used to illuminate the pattern, component tolerances, dust in the optics, and any other effects that would change video amplitude over a long term. The second function of the video processing circuits is to minimize shading, the result of a non-flat illumination field creating a bowed video baseline. Finally, after automatic gain control and shading elimination, the video signal is quantized into a binary digital signal. Nominally, the quantizing level is set to 50%.

The output of the video processing circuits 152 is fed to a scan storage unit 154, a prelook unit 156 and a skew unit 158. The scan storage unit 154 consists of a 2048 stage shift register. Data is entered in the shift register during one scan, and appears on the output exactly one scan later. Timing and control is designed to recycle every 2049 bits with a 1 bit dead time. There are 1728 elements active on the signal from the camera and 321 bits of blanking are used for data processing later in the block diagram.

The purpose of the prelook unit 156 is to gate out of the camera video signal incomplete patterns prior to comparative analysis. These incomplete patterns may be either in the beginning or end of a scan and are due to a number of causes. For example, the camera may be aligned in such a manner that the first pattern elements fall in the middle of an opaque slit. Also, some patterns may actually have incomplete slits around the edges. Or finally, a compare error may be generated on the pattern trailing edge, due to absence of a neighbor pattern for comparison. With the prelook circuit, the video from video processing circuits 152 are analyzed, starting and ending locations are stored, and then when video emerges from the scan storage during the next scan, the unwanted video is removed via an "And" gate 160.

The functioning of the skew unit 158 is illustrated with respect to FIGS. 12 and 13. Two scans, A and B, that just touch or just miss the top of a slit 162 are shown. Signal 164 is the real time scan from Scan A emerging from the video processing circuits 152 and signal 166 is the delayed scan from Scan B emerging from the scan storage circuit 154. Presence of a pulse in Scan A and absence of a pulse in Scan B causes the skew unit 158 to generate a signal 170 labeled "New" which has a pulse 168 indicative of this difference. Analysis of the signal 170 with respect to a signal 172 related to half the scan time gives an indication whether the camera and pattern are aligned. If the camera is misaligned, either a CW or CCW light 174 and 176 respectively will flash continually, but when aligned, both indicators will sporadically flash.

The "New" signal 170 from the skew unit 158 is fed into a classification circuit 178. Two decisions must be made in the classification circuit 178. First, the type of pattern, whether dot or line, must be determined and next, if it is a line pattern, a rough estimate of element-to-element or "a" spacing must be established. To establish a type of pattern, blank scans are monitored. If blank scans occur within the pattern, then the plate is classified as a dot plate, since no blank scans will occur in a line pattern. By utilizing the "New" signal 170 and measuring distance to the next pattern element a number of times, a good indication of ½ of the "a" spacing is achieved. This value doubled is used in the comparative logic as a starting point, but is continually modified in a servo module 180, to follow "a" spacing variations. The classification 178 is primed by an outside signal 182 indicating when classification should occur. During classification, the "a" spacing is displayed for operator perusal.

Output from the "And" gate 160 is also fed into two variable length shift registers 184 and 186. These shift registers 184 and 186 are the center of the comparative logic. One register 184 has a maximum length of 32 stages and the other register 186 has a maximum length of 192 stages. In a standard shift register, all stages contain information, and when one bit is loaded at the serial input, all stages are triggered, and the last stage is dumped. In a FIFO type of register such as used in the present embodiment, the loading of the input is independent of the unloading of the output, so the amount of information contained within the register is variable. For example, data may be entered in bursts, and removed at uniform rates, the only requirement being that average rates over a period of time be identical. In the present embodiment, the first complete scan pattern is stored in the 192 stage register 186, (nominally 80 stages are used) and then when the second scan pattern is received, the first and second scan patterns are shifted in parallel to the comparative logic. The register inputs are controlled by the input logic and the outputs are controlled by the servo module 180. Information when loaded will trickle into the registers as far as possible until it hits a stage that contains information. The first element loaded appears on the output in a manner of nanoseconds.

Outputs from each of the registers 184 and 186 are fed into two leading edge detector circuits 188 and 190. These circuits look for the leading edge of a scan pattern defined as the transition from a clear mask area, to an opaque area of a pattern element. Once this transition is detected, the signal is sent to the servo module 180 to determine if the transition is at the correct location to be the start of a scan pattern. Within each leading edge detector circuit there is filtering to compensate for the roughness of the edges of the pattern elements.

The servo module 180 is the control center for the system. Inputs to the servo module 180 come from the two leading edge detectors and information from the classificaton circuit 178 including type and initial "a" spacing. The servo module 180 then in turn controls the output of the two registers 184 and 186, updates the "a" spacing, and enables the comparative output logic. Initially, the first pattern is loaded into both registers 184 and 186 but is held only in the 192 stage register 186. The second pattern is loaded into both registers trickling to the end of the 32 stage register 184 but bumping up against the first pattern in the 192 stage register 186. When the leading edge of the second pattern is detected at the end of the 32 stage register 184, the outputs from both registers are stepped in unison, and the comparative logic is turned on. This process continues until end of scan. To allow for small variations of "a" spacing or for quantizing errors, the output of either shift register may be frozen, until the servo logic determines that both register outputs contain pattern leading edges. Within the servo logic, the "a" spacing is constantly updated to aid in the determination that an edge is a pattern leading edge, and not some defect.

Outputs from the two registers 184 and 186 and from the servo module 180 are fed into a correlation algorithm circuit 194. This circuit 194 consists of a full adder that may be wired to act as a majority gate. In this application, the adder looks at 5 pattern elements of both registers 184 and 186 in parallel, and if 3 or more pairs are identical, then a miscorrelation signal is not generated. A miscorrelation signal is only generated when less than 3 pairs match.

The sensitivity of the basic compare circuit in the correlation algorithm circuit 194 may be modified by manual activation at a mode switch 196. One of the 5 bits of pattern element information may be either forced true or false thereby changing the basic 3/5 to either 2/4 or ¾ weighting. Also, via the switch 196, the compare circuit may look at either 5 adjacent pattern elements or 5 alternately spaced pattern elements. Another option is to select one mode for the clear mask area and another mode for the opaque mask area. FIG. 14 is a table showing the various modes available. The first number in the top row and the left hand side column indicates whether each pattern element (1) or every other pattern element (½) is analyzed. The second number indicates the correlation level required to be acceptable. The numbers in the top row refer to the opaque pattern element, and the numbers down the left side refer to the clear areas of the pattern. For example, Mode 7 sets the following criteria.

Clear area of pattern all pattern elements are analyzed, and in any group of 4, three pairs must be identical.

Opaque area of pattern only every other pattern element is analyzed and in any group of 5 pattern elements, three pairs must be identical.

False miscorrelation at or near the ends of a pattern element may be caused by skew introduced by the mechanical motion of the camera, minute variations of element lengths, or by normal quantizing errors on the video signal. To eliminate these false errors, it is required that for a miscorrelation to be identified as an error, it must occur in two consecutive scans at the same location. This is accomplished by first loading a miscorrelation signal into a scan storage shift register 198, and if on the following scan another miscorrelation occurs at some spot, an "And" gate 200 is satisfied and an error is indicated.

To aid an operator in monitoring the performance of the scanner, a two digit display 202 connected to a multiplexer 204 is provided. During initialization, the initial "a" spacing, fed from the classification circuit 178, is displayed, but once the unit starts scanning the full pattern, the updated "a" spacing from the servo module 180 is displayed. The multiplexer 204 is controlled by the prime signal 192 to gate the proper signals to the display.

In the foregoing digital embodiment of FIG. 11, several logic circuits are associated with the scan storage 154, prelook 156, skew 158, classification 178, servo 180 and correlation algorithms 194. These special circuits will now be described with respect to FIGS. 15 to 27. In this description, the mechanical motion of the camera will be referred to as "vertical" scan and the electronic scan as "horizontal".

Prelook and Scan Storage

Figure 15:
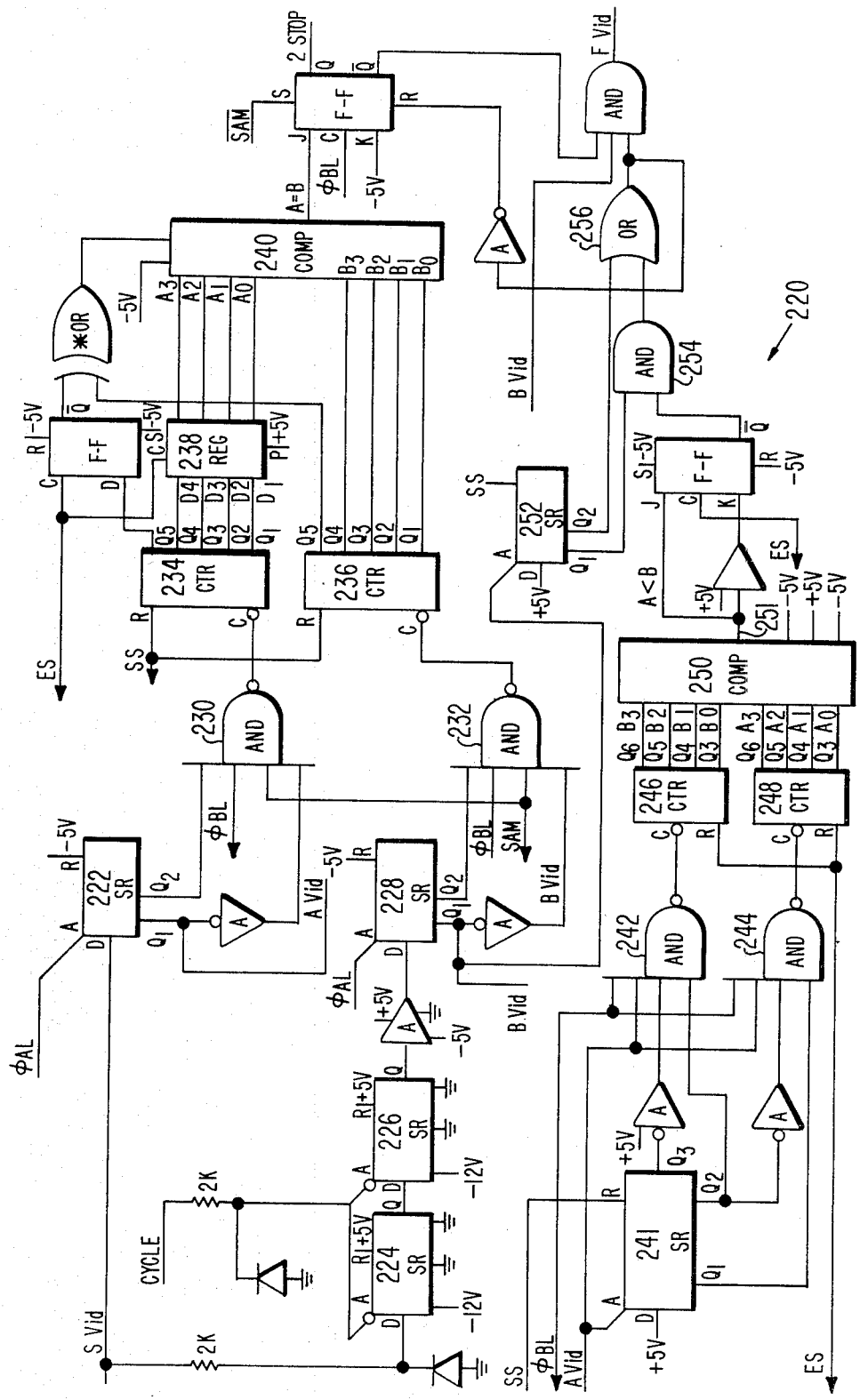
FIG. 15 is a circuit diagram of prelook and scan storage sections.
Figure 16:
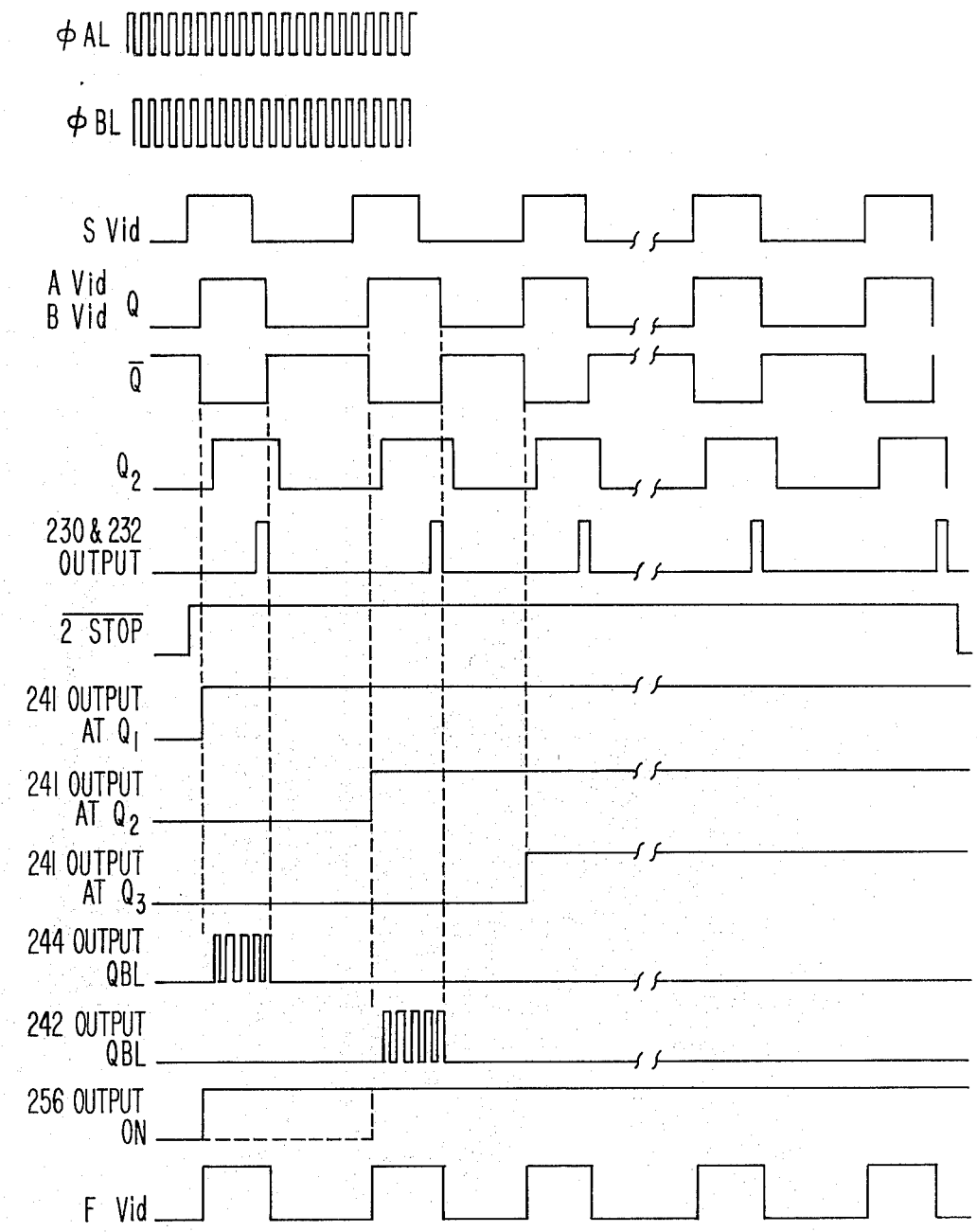
FIG. 16 is a schematic diagram showing waveforms associated with the circuit of FIG. 15.

The prelook 156, scan storage 154 and associated circuitry 220, shown in FIG. 15, is intended to prevent the system from creating false errors due to two conditions. First, since the system works on the principle of comparing one module of video with the next, there must be determination of when the video signal scan begins and when it ends so that there is no attempt to compare an existing module to a nonexisting module. The '2 STOP' signal provides this information, as shown in FIG. 16. Second, there may be an error condition created because the first input slit signal is narrower than the second. This first narrow pulse can be due to a possible partial slit at the corners of the plate or because of plate design. The system will, therefore, not begin to compare signals until the widest slit of the first two is recognized. The 'FVid' signal, shown in FIG. 16 along with other waveforms associated with the circuit 220, is therefore the resulting corrected video seen after the above conditions have been met.

The scan storage circuitry, shown in FIG. 15, works as follows. The 'SVid' signal, from either the Reticon array or the video generator, inputs a two stage shift register 222 and a 1024 stage shift register 224. The register 224 plus another similar register 226 provide a total of 2048 stages or one complete scan of delay (one scan of video equals 1728 stages or video plus 320 stages of blanking). The video into the register 222 and the delayed video at another two stage shift register 228 are now synchronized with a clock signal '$\phi$AL' to insure good alignment. The two video signals, real time and delayed, are labeled 'AVid' and 'BVid', respectively. 'And' gates 230 and 232 now provide one '$\phi$BL' clock pulse at the trailing edge of each video signal, as shown in FIG. 16. Two binary counter 234 and 236, provide a count of input pulses representing the number of video signals per scan. At the end of a scan, the count of the total number of 'AVid' video signals is stored in a digital latch 238. The output of the latched count and the one scan delayed video count are compared with each other at a digital comparator 240. Only when the A=B condition is reached will the output go high, generating '2 STOP', which in turn will disable an error detector. To determine which of the first two input slits to start operating on, two gates 242, 244 allow, the 246 and 248 counters to measure the width of the first two video signals. The digital comparator 250 compares the resultant count each scan. If the first slit 'A' inputs to the comparator 250 are less than the second slit 'B' inputs, the comparator output 251 will go high at that time. If 'A' is not less than the 'B', the comparator output 251 will stay low. In other words, if the first video signal is narrower in width (A<B) than the second video signal, the system will operate on the second video received. If the first video received is equal or greater than the second, then the system will begin operating at the first video. A register 252 is clocked with 'BVid' and only transfers the high input to $Q_1$ and $Q_2$ at the second 'BVid'. If the first video had previously been selected as good, the $Q_1$ output would be passed through the gate 254. If it was bad, the system will wait for the second video signal transfer to the $Q_2$ signal to 254. The output of 254 is conjunction with the '2 STOP' output, determines the output video to the comparator.

Skew

Figure 17:
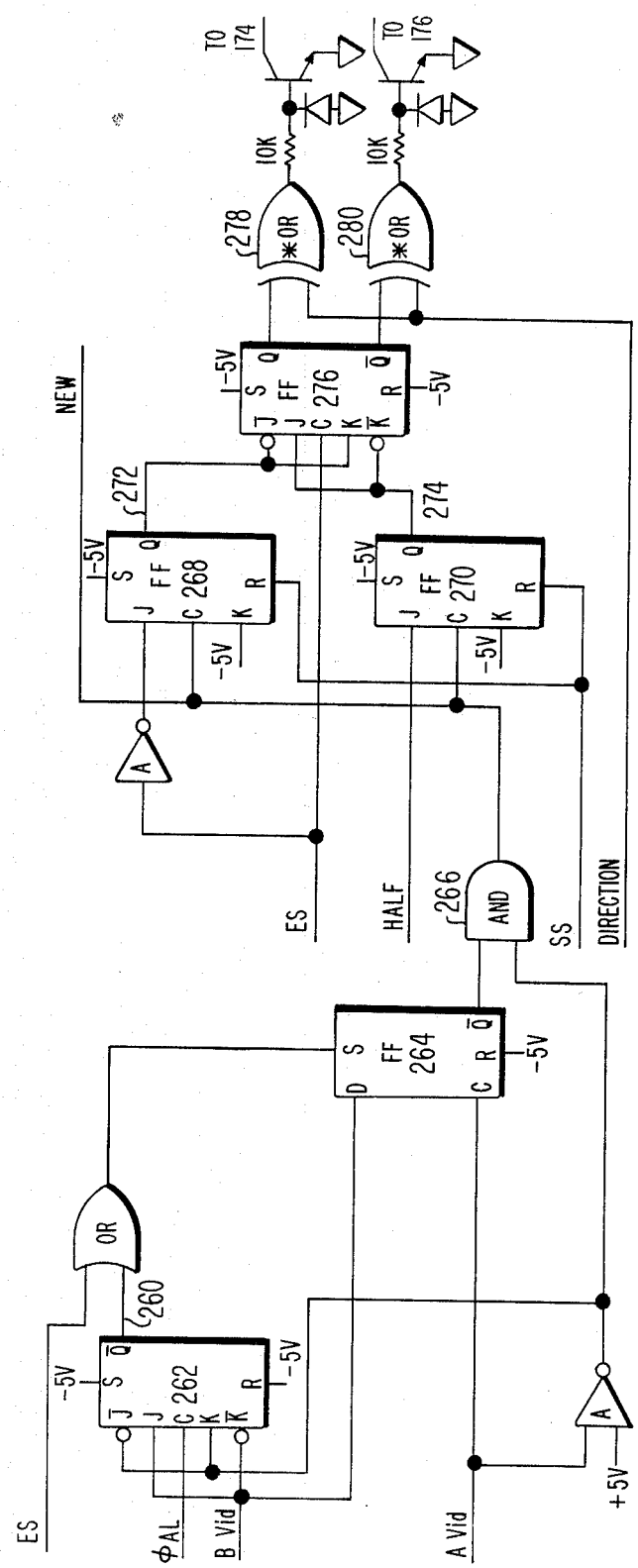
FIG. 17 is a circuit diagram of a skew correction circuit.
Figure 18:
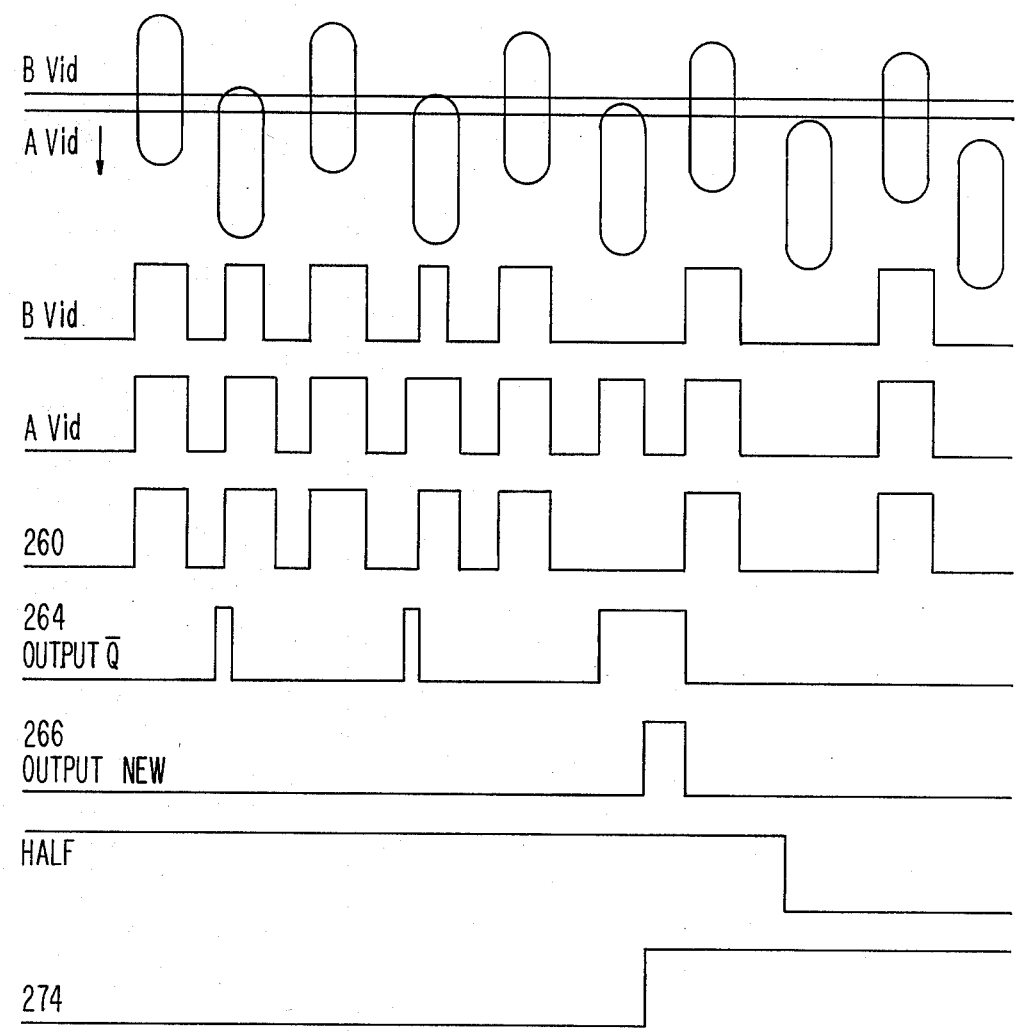
FIG. 18 is a schematic diagram showing waveforms associated with the circuit of FIG. 17.

The skew correction circuit 158 shown in FIG. 17 with associated waveforms shown in FIG. 18, is intended to provide an indication, without the use of an oscilloscope, as to when the plate to be scanned is aligned properly. It is important to insure that when the camera is mechanically moved across the plate, the set of similar slits all first appear in the same electronic scan. The top portion of FIG. 18 shows the video as viewed with a misaligned plate. The skew indicator lights 174 and 176, see FIG. 11, operate at all times and indicate each time there is a 'NEW' signal or a condition when the delayed video 'BVid' does not show a slit and the current scan does. A 'NEW' signal may be generated either at the beginning or end of a horizontal scan with the indicator light, 174 or 176, showing which side of the video scan that the slit was missed. Since there is a difference in 'NEW' signals depending on when the camera is moving up or down, the indicator lights are used as follows. When the camera is focused and positioned at the top or bottom center location of the plate and is manually allowed to move in the vertical direction (if the camera is moving up) the plate is rotated slightly until the 'left' indicator light is just flickering. In the down direction the plate is adjusted so that the 'right' indicator light is just flickering. When the plate is properly aligned the above conditions will exist for the up and down camera motion.

In understanding the skew circuit operation it must be noted that the objective of the circuit 158 is to generate a signal 'NEW' any time the condition arises that the 'AVid' signal and the scan 'BVid' do not agree, as shown in FIG. 18. The circuit 158 also will indicate at which part of the horizontal scan the 'NEW' signal occured. The output 260 of the J-K flip-flop 262 will toggle high only when both the 'AVid' and 'BVid' signals are identically true. This output 260 will not go low until both inputs are identically false. A type D flip-flop 264 output will be toggled high by 'AVid' only when the 'BVid' and the set input are low. A gate 266 will now only pass this high when 'AVid' is low. The resulting 'NEW' signal, as shown in FIG. 18, will appear at either the beginning half or the end half of the horizontal scan and is therefore an indication of the time that 'AVid' and 'BVid' do not agree. Two J-K flip-flops 268 and 270 determine if the 'NEW' signal has appeared at the beginning or end of the scan. Anytime a 'NEW' signal appears, the outputs 272 and 274 from the flip-flops 268 and 270 will be toggled high. The 'Half' signal which is high for half the horizontal scan allows the output 274 to go high at the time of a 'NEW' signal only during the first half of the scan. And, likewise, the output 272 will go high only during the second half of the scan. A J-K flip-flop 276 will now only change state at the end of the scans if the J-K inputs are dissimilar. Two exclusive OR gates 278 and 280 will change the selection of the indicator lamp 174 or 176, depending on the direction of the vertical scan.

Classification

Figure 19:
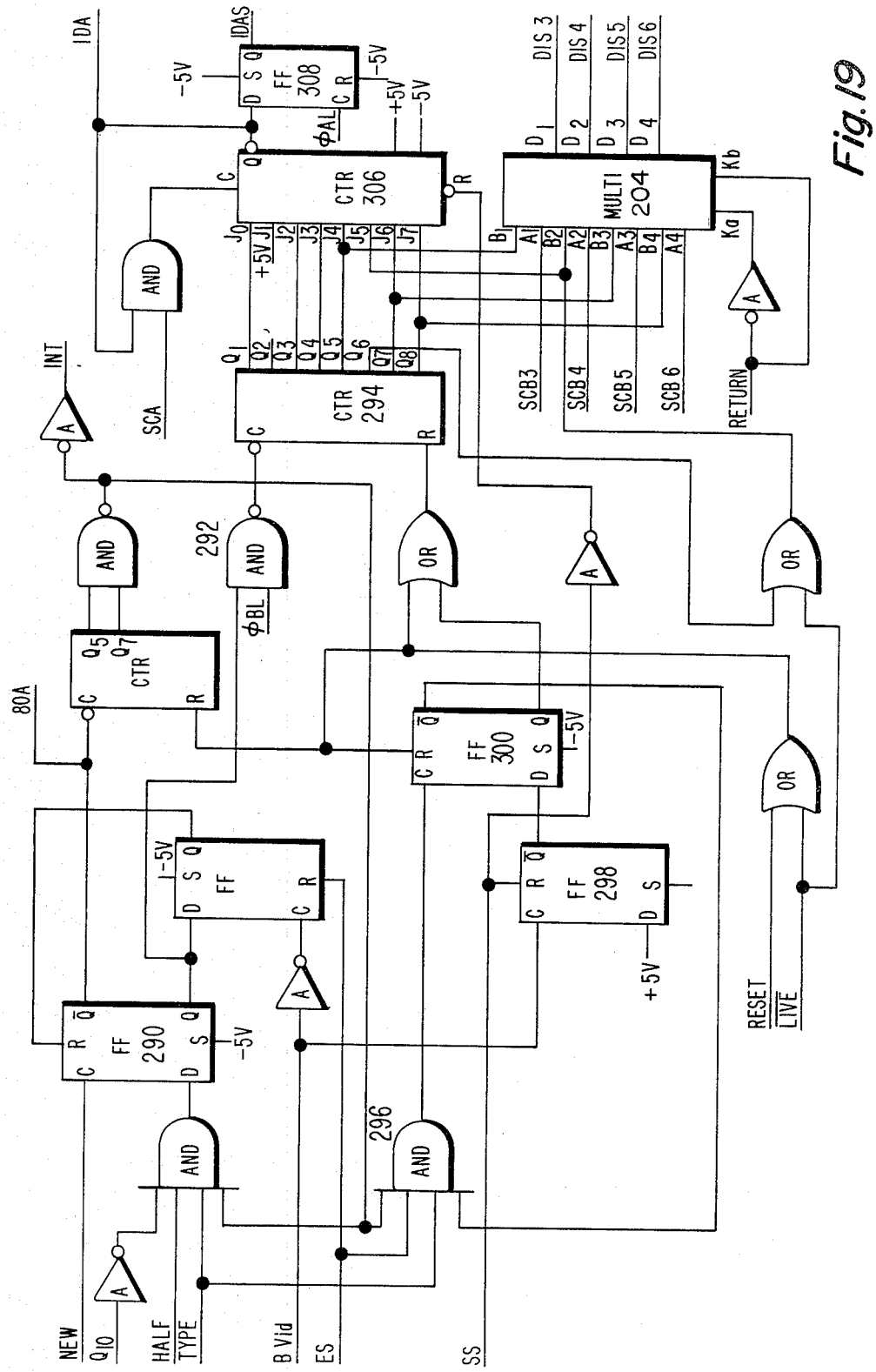
FIG. 19 is a circuit diagram of a classification circuit.
Figure 20:
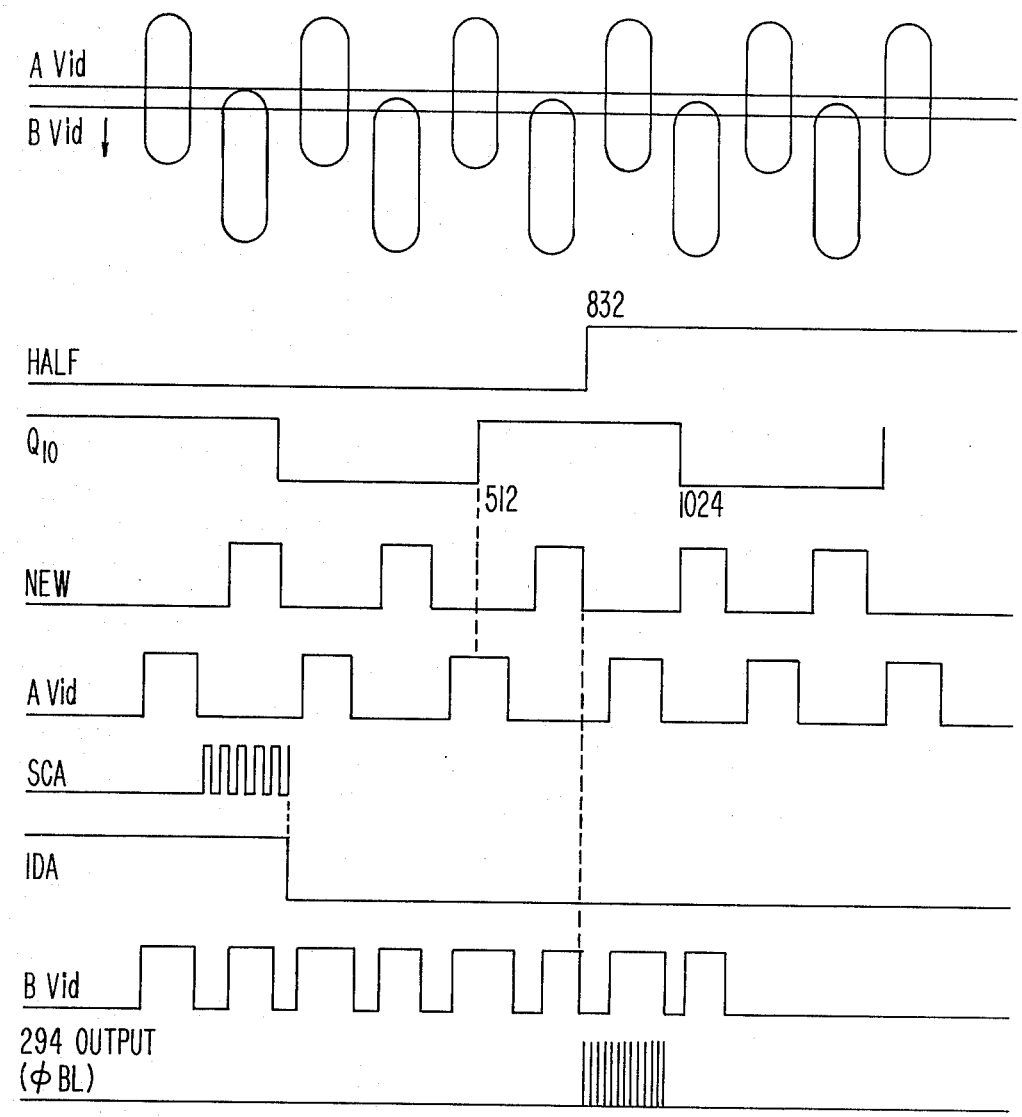
FIG. 20 is a schematic diagram showing waveforms associated with the circuit of FIG. 19.

Two decisions must be made in the classification circuit 178, shown in FIG. 19. First, it must decide the type of working plate pattern; whether it has dots or slits. Second, if it is a slit pattern, the circuit must give a rough estimate of slit-to-slit 'a' spacing. To determine the type of pattern, blank scans are monitored. If blanks scans occur within the pattern, then the plate is classified as a dot pattern plate. By utilizing the 'NEW' signal, and measuring the distance to the next slit a number of times, a good indication of $\frac{1}{2}$ of the 'a' spacing is achieved. This value, doubled, will be used in the comparative logic as a starting point, but will be continually modified during scanning to follow 'a' spacing variations. The circuit is primed by an outside signal as to when classification should occur. During classification the 'a' spacing is displayed for operator perusal.

The circuit 178 requires that the camera be in the return mode and returning in the vertical direction along the left skirt of the pattern. When the above conditions are met the 'TYPE' input will be high allowing a high at the time of '$Q_{10}$' and 'HALF', which is the approximate center of the video scan shown in FIG. 20. Only at this time can a 'NEW' signal toggle the flip-flop 290 low. The 'NEW' signal, as described with respect to the skew circuit, indicates each time the camera "vertical" scan senses a slit beginning. In this case, only, the center of horizontal scan is considered. Immediately after a 'NEW' signal until the trailing edge of 'BVid', shown in FIG. 2, gate 292 is enabled allowing $\phi BL$' to toggle a binary counter 294. This count is repeated and accumulated for 80 scans. Since the count from between video trailing edges is a measure of $\frac{1}{2}$ the 'a' spacing and since it is desirable to have an average 'a' spacing measurement the calculation of $$\frac{N \times 80}{64}$$

(where N=number of '$\phi BL$' clocks) is made. This is accomplished by taking the 80 accumulated counts starting at $Q_7$ instead of $Q_1$. This effectively divides the $N \times 80$ count by 64 and thus provides the average 'a' spacing.

Since the system is constantly aligning one video black to white signal with the next, in the case of the plate with slits, it is important to know the relative distance between slits so that there is no attempt to look in on the intermediate webbings. With the dot pattern plate this is of no concern since there are no intermediate signals such as between slits. Gate 296 and flip-flops 298 and 300 are used to determine if the plate being scanned is a dot or slit pattern. If the conditions of the gate 296 are met (return mode), the 'ES' signal will clock flip-flop 300. A type 'D' flip-flop 298, which is reset each 'SS', will be clocked on the the very first video signal causing its output to go low. At the end of the scan the 'ES' signal will clock the flip-flop 300 but '$\overline{Q}$' will remain high since the 'D' input is low. In the event that for one full-scan there is no video signal, which is the case with a dot pattern plate, the output 302 will remain high for the entire scan. At the time of the 'ES' signal the $\overline{Q}$ output 304 from the flip-flop 300 will be toggled low preventing any further 'ES' signals from passing through the gate 296. The system has now determined that it is scanning a dot pattern plate. For a dot pattern plate a binary down counter 306 is set to an initial count, at the start of each scan during this learning mode, by way of the jam inputs J0 to J2 of the counter 306. In the case of the dot pattern plate the jam inputs will be zero and the minimum count of two will be set, since $J_1$ is tied high. In the case of the slit pattern plate the binary counter 294 will not reset and will provide an 'a' spacing count. The down counter 306, having been set, will count down with the 'SCA' signal (QBL after the first video signal). Once the counter reaches zero, 'IDA' will go low blocking any further clocking of the counter 306 until the next scan. Once the learning period is over, the count will remain the same.

The 'IDA' input to a flip-flop 308 is synchronized with 'QAL' to create the 'IDAS' that goes to the servo section 180 to control the time when a video comparison is to begin as explained with respect to that section. The 'IDA' signal, once it goes low allows a 'Zone 2' signal to pass through a gate to form a 'Test' signal.

Multiplexer 204 is a quad AND/OR select gate which is used to control the front panel display. In the return mode 'RETURN' is high, which allows only the $B_1$ to $B_4$ inputs to be passed to a front panel display indicating the count of the counter 294. In the 'GO' mode the 'Ka' is high therefore selecting for display only the $A_1$ to $A_4$ inputs which are a constantly updated indication of the A-spacing.

Servo

This servo module 180 is the control center of the system. Four portions of the servo circuitry are shown in FIGS. 21, 22, 23 and 24. Inputs to the servo 180 are the two leading edge detectors, and information from the classification circuit, type and A-spacing. The servo 180 then in turn controls the output of the two FIFO's 184 and 186 and enables the comparative output logic from the correlation algorithms 194. Referring to the servo circuitry, the 'IWB' (input white to black) and the 'DWB' (delayed white to black) signals are compared at an AND gate 320, shown in FIG. 23, when the 'TEST' signal, as derived from the variable A-spacing section goes high and allows this comparison. The signal output from the gate 320 is synchronized with 'QAL' at a flip-flop 322 to provide the signal 'Match'. This 'Match' signal will be high only when '$\overline{\text{IWB}}$' and 'DWB' correspond. At a gate 324 the '$\overline{\text{IWB}}$' and 'DWB' are 'Anded' at the time of 'TEST'. While vertically scanning the slit pattern there is an intermediate slit that appears between the horizontal scan of the two main slits. The main slits are defined as 1A, 2A, and 3A. The intermediate slits are defined as 1B, 2B, and 3B. The output 'DLIA' (delayed leads Input A) signal for 1A compares the 'DWB' signal with the '$\overline{\text{IWB}}$' signal to determine if the delayed video leads the input video. Conversely, gate 330 compares '$\overline{\text{DWB}}$' and 'IWB' to determine if the input video leads the delayed video. These two signals are ORed in a gate 326 to provide the 'MisM' signal indicating a mismatch of the alignment of the 2 A-Video signals. Both the 'Match' and 'MisM' signals are used in determining the 'a' spacing in the circuit of FIG. 24. The 'ILD' signal from the gate 328 as developed from either the gate 330 or gate 360 and, when low, prevents any output advance of the 32 stage FIFO 184 until the delayed video is aligned with the initial video.

Figure 21:
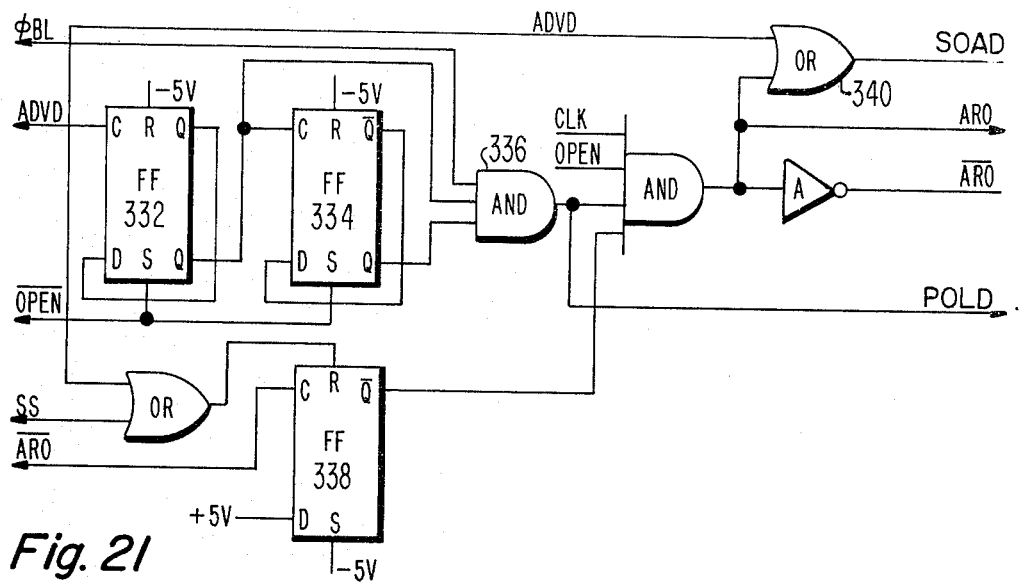
FIGS. 21, 22, 23 and 24 are circuit diagrams of a servo module.

The signals 'ARO', 'Pold', and 'SOAD' are developed by the circuit of FIG. 21. These three signals respectively determine when the data at the FIFO 184 is to be put into the parallel loading input of the parallel to serial converter, and the serial output to the leading edge detector 188. As can be seen in FIG. 21 the 'ADVD' (advanced delayed A-video) signal, which is a 'QAL' clock at times of 'DLI' and 'OPEN', both advances the data through the leading edge detector and clocks the type 'D', flip-flop 332. At the time 'OPEN' is low the 'ADVD' signal goes through a divide by 4 at the flip-flops 332 and 334. The inputs to an 'And' gate 336 which are 'ADVD/2', 'ADVD/4', and 'QBL' for the 'Pold' signal which is also shown in FIG. 21 is a 'QBL/4' clock. At the time of 'OPEN', 'POLD' and with the $\overline{Q}$ output from a flip-flop 338 high, the 1.5 MHz 'CLK' signal will form the 'ARO' signal which will release the FIFO 184 data parallel loading. The trailing edge of the 'ARO' signal will clock the $\overline{Q}$ output from the flip-flop 338 low blocking any further generation of this signal until the next 'ADVD' or 'SS' reset to the flip-flop 338. The 'SOAD' signal generated at a gate 340 is used to clock serially the data parallel loaded at 'POLD'.

There are three conditions when the data in the 192 stage FIFO 186 (delayed video) must be frozen, so that the 32 stage FIFO 184 (input video) can be aligned. First, when the first video signal is received at both FIFO's it should be passed through the initial stage but frozen at the delayed stage. It is not until the second 'A' slit is received that the data in the 192 stage FIFO 186 can be released for comparison. Second, each time the delayed video and the input video are compared, they must align before a comparison can be made. Third, the intermediate data defined as the B slit must also be a match before a comparison can be made.

Figure 22:
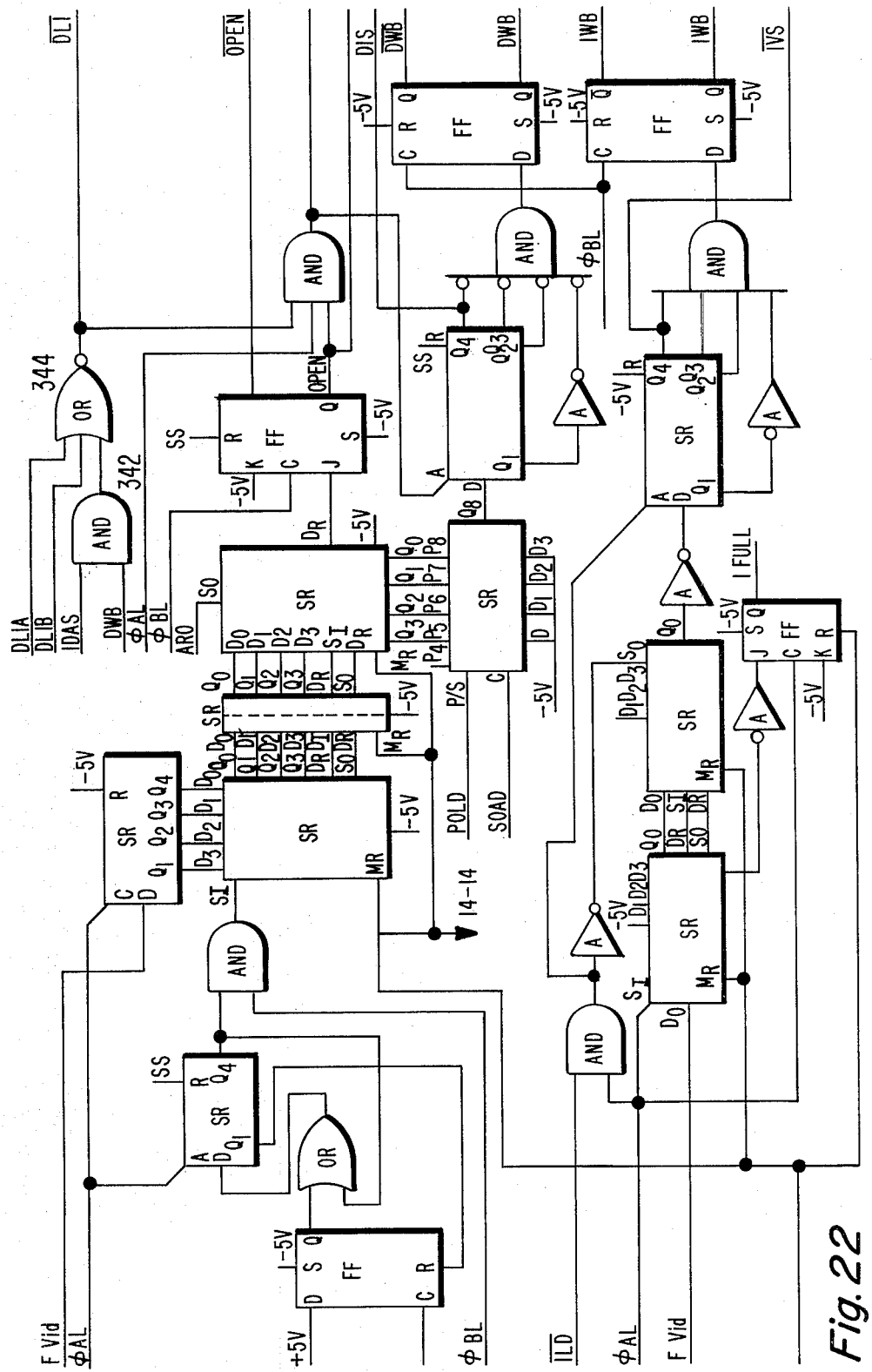
Figure 24:
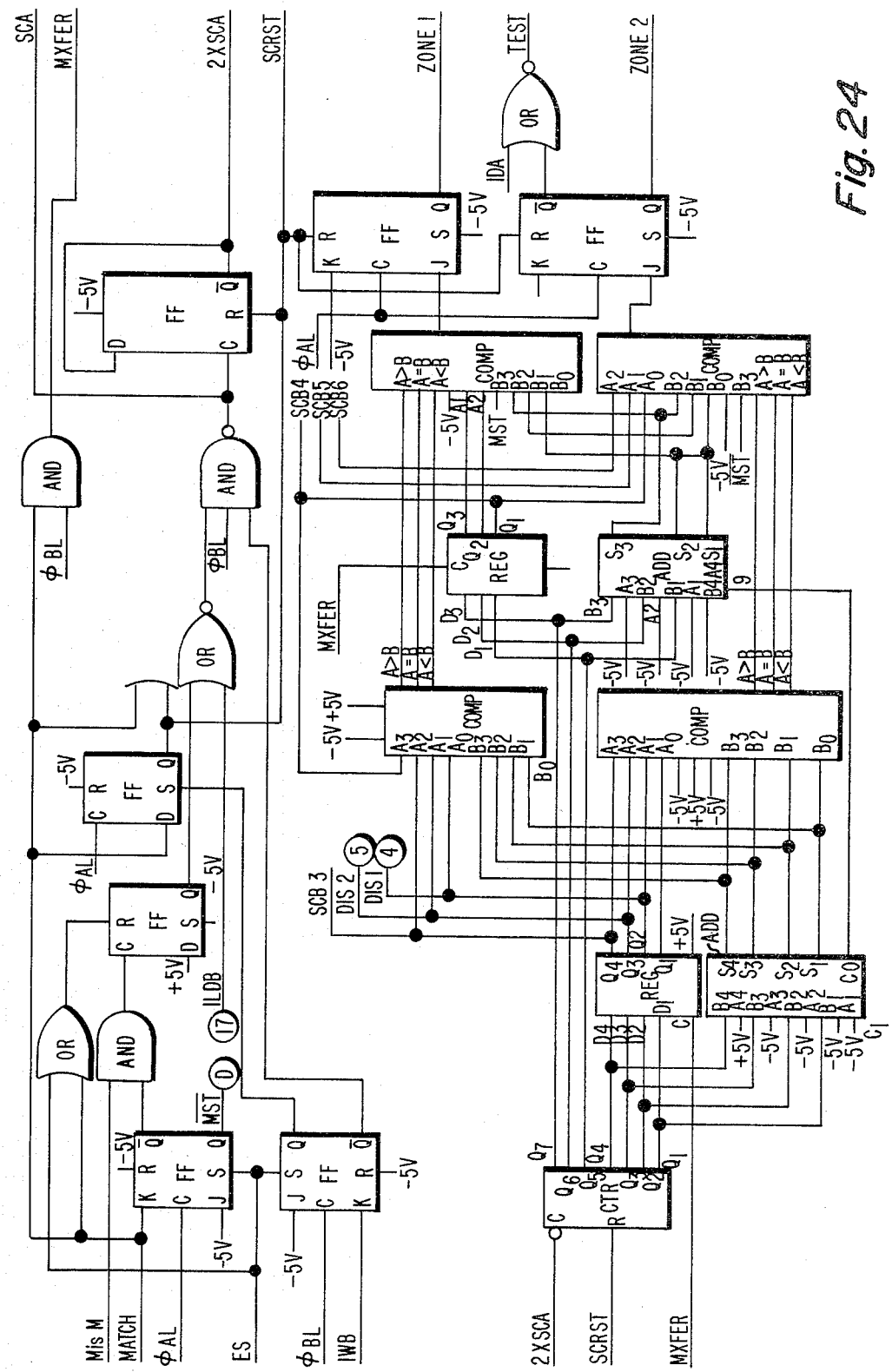

The control of this data alignment for the initial conditions is accomplished at a gate 342, shown in FIG. 22. The 'IDAS' signal, which is generated in the circuit of FIG. 19 and is a result of the initial 'a' spacing, as described with respect to that circuit, will be high until the initial count for the 'a' spacing is reached. By this time, the first 'DWB' signal has already been passed through this gate 342. The 'IDAS' signal will go low just before another 'DWB' signal can be received. Since initially 'DLIA' and 'DLIB' are low, the very first 'DWB' will cause 'DLI' to go low preventing any further 'ADVD' signals. Once 'IDAS' goes low, a gate 344 is free to pass either of the 'DLIA' or 'DLIB' signals. Since they have not yet been generated 'DLI' will go high allowing the 'AVID' signal to advance the data.

The 'DLIA' and 'DLIB' which were generated at the gates 330 and 369 will go high any time the delayed video leads the initial video. A high at either of these signals causes 'DLI' to go low, stopping any further advancing of data until the delay and input video signals align. Thus condition is repeated for every legitimate video signal received so that an accurate comparison of video can be made in determining and error condition. The use of the initial 'a' spacing 'IDAS' signal prevented any attempt of the system to initially lock in on an error or intermediate 'B' slit.

Figure 23:
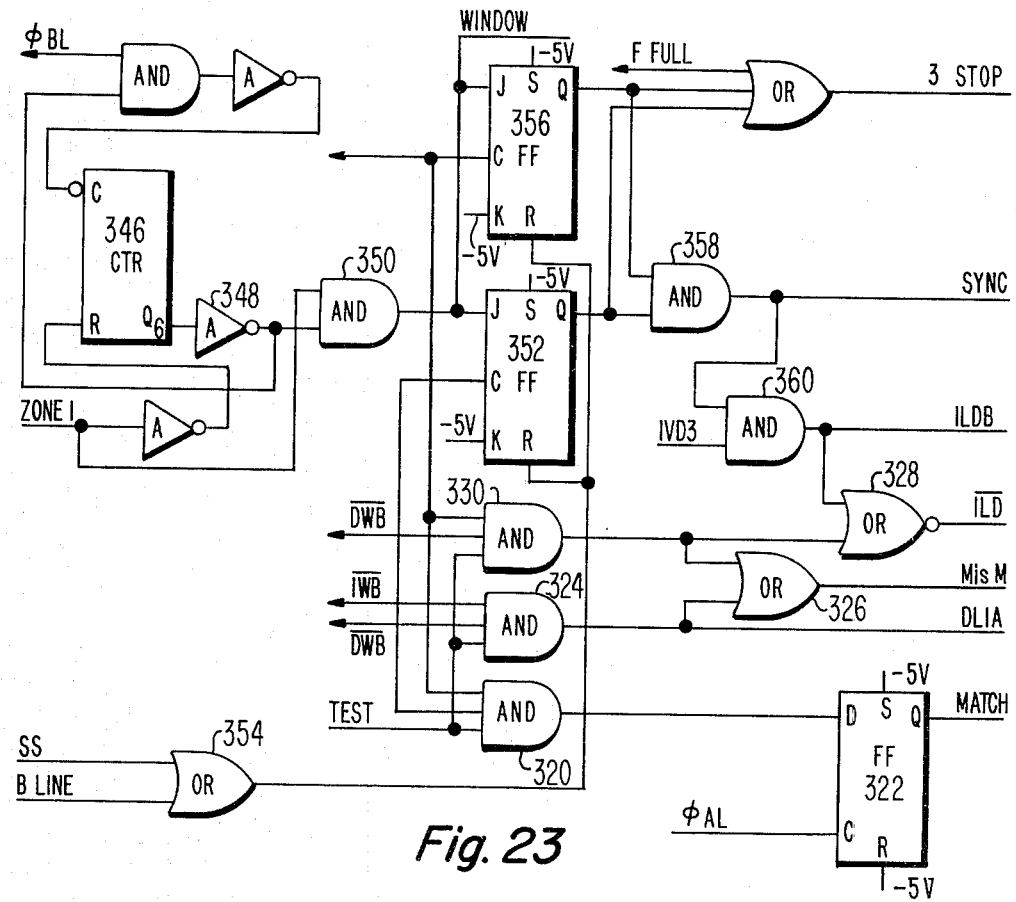

The circuit, as shown in FIG. 23, generates the 'window' 3 'stop' 'Sync' and 'ILDB' which determined the vicinity of 'B' video with the 'window' signal and then as soon as either the 'IVS' or 'DVS'0 video is received lock the system until these two signals align and then releases the system for a video comparison. There is also a safety factor in that as soon as 'IVS' or 'DVS' is detected, if the other comparison does not appear within 8 clocks the system will be released. The circuit functions as follows; referring to FIG. 23, at the time of a high 'ZONE' 1 a binary counter 346 will go high after 16 '$\phi$B2' clocks. A gate 348 then goes low blocking any further count. A gate 350, provides a high level for 16 counts at the start of 'ZONE' 1 and is labeled 'window' since it encompasses the time that the 'B' video signal is present. At the time of a 'DWB' which is the input clock to a flip-flop 352, if the window exists the Q output of the flip-flop 352 will go high and remain high until a reset is received from a gate 354. Likewise, if the 'IWB' clocks a flip-flop 356 during the 'window' output of the flip-flop 352 will go high until both inputs to a gate 358 are high. Once the outputs of flip-flops 352 and 356 both go high a 'SYNC' signal goes to the correlation algorithm circuits 194. At the circuit of FIG. 25, the high 'SYNC' signal at gates 368 and 369 will be inhibited since 'IVD3' and 'DVD3' are still low, allowing the shift registers 378 and 380 to be advanced. Either 'IVD3' or 'DVD3' will block the clocking of the shift registers 378 and 380. When both 'IVD3' and 'DVD3' occur a gate 381 will pass '$\phi$BL', allowing the 'B line' signal to reset the J-K flip flops 352 and 356 of FIG. 23. This causes the 'SYNC' signal to go low allowing the gates 374 and 376 to once again clock the shift registers. It should also be noted that at the time of a high at either flip-flops 352 or 365 or the 'F Full' signals of FIG. 23 the '3 stop' signal will block any attempt at an error generation in the circuit of FIG. 26.

Correlation Algorithm

Figure 25:
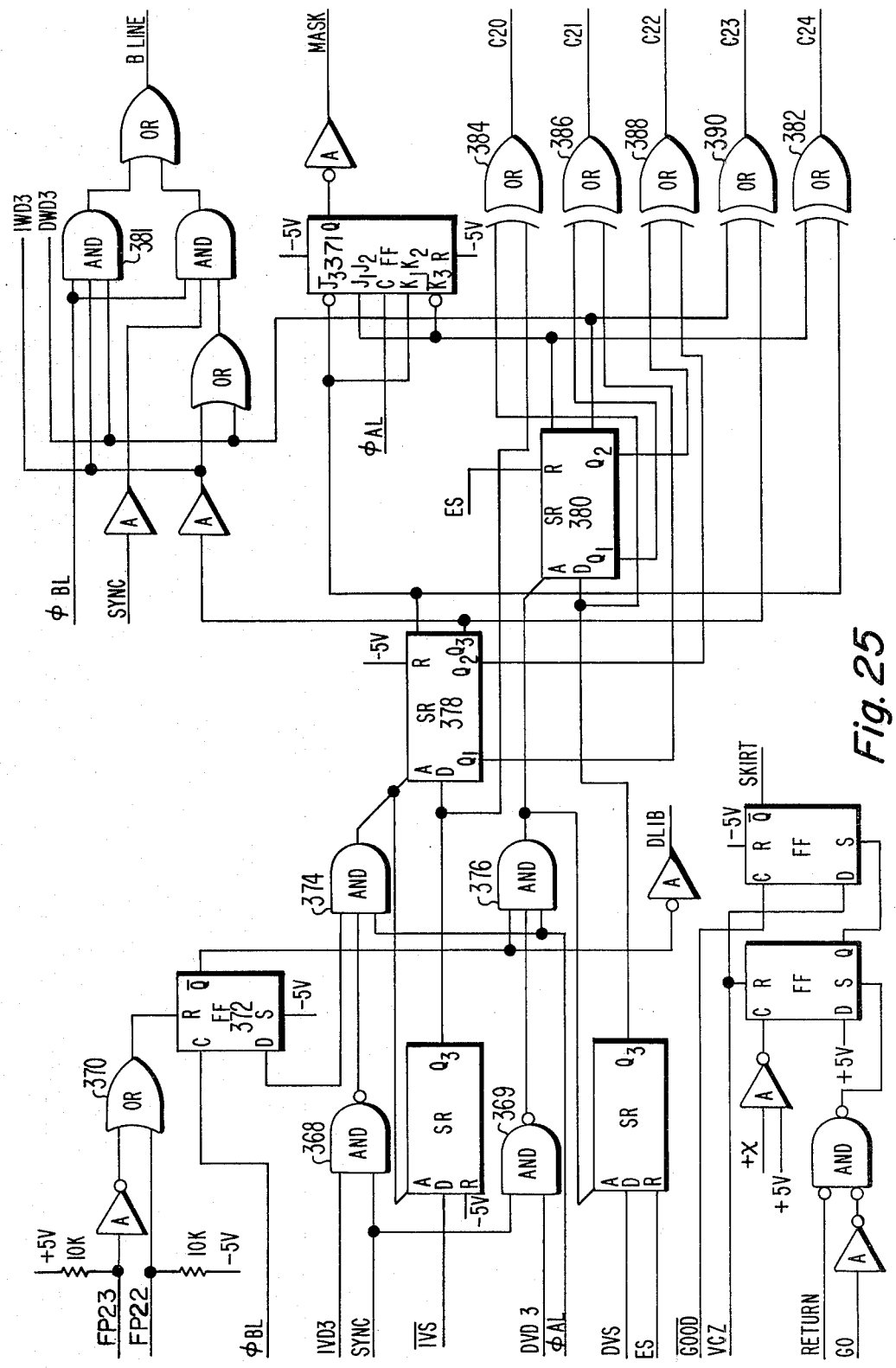
FIGS. 25 and 26 are circuit diagrams of a correlation algorithm section.
Figure 26:
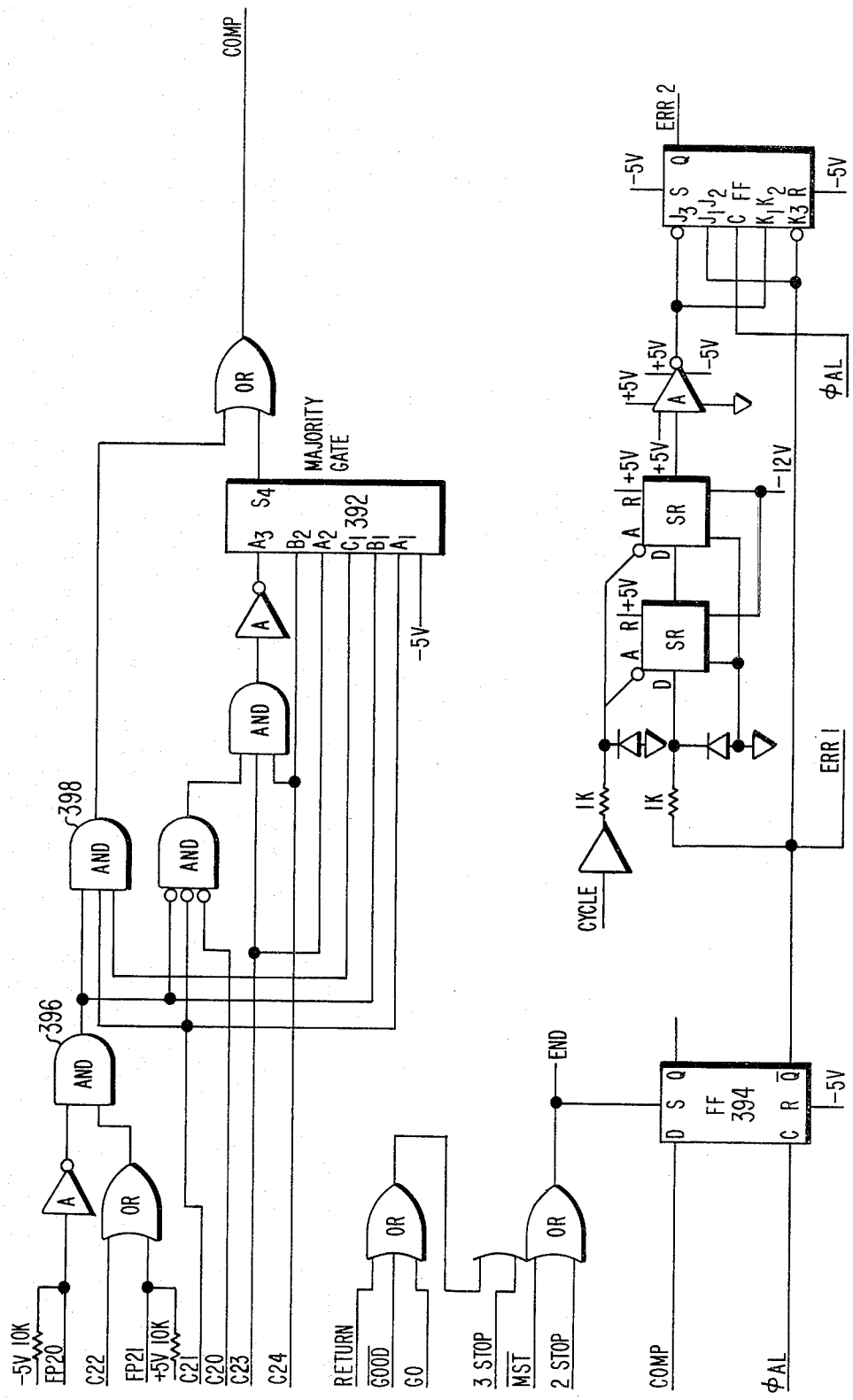

The object of the correlation algorithm circuit shown in FIG. 25 is to set a criteria for the comparison of the 'IVS' and delayed 'DVS' video signals after all efforts have been made for proper alignment. Since there are variations in the video pattern, that may or may not be of concern, there is a front panel mounted hexadecimal (hex) weighting switch 196 allowing an individual to select the degree of error sensitivity both for opaque and translucent areas of the plate. For instance, as seen in the chart of FIG. 14 for both the opaque and translucent areas there are two options. Either every $\phi$AL clock or every other '$\phi$AL' clock of video can be compared as indicated on the chart as '1' or '$\frac{1}{2}$'; also a weighting factor is introduced for determining to what extent a signal will be considered an error. A 2/4 indicates that of every 4 video picture element pairs received at least 2 of these must compare to be considered a good signal. Likewise, the 3/5 and ¾ settings indicate, of 5 or 4 respective element pairs received, 3 must compare, otherwise there is an error indication. The front panel hex switch 196, therefore, provides 16 options, with the 'F' position being the most sensitive, in that it compares every clock of video and requires a 3/5 ratio for a good signal. The 'O' position is the least sensitive since it compares every other clock of video and requires that only a 2/4 ratio of video comparison to have an acceptable signal.

In understanding the circuit of FIG. 25 it is first assumed that the hex switch is in the 'F' position. A 'MASK' signal from a flip-flop 371, which is generated whenever both video samples are on clear (mask) data, is connected to the common of the hex switch. In the case of the 'F' position all four of the hex FP outputs will follow the mask signal. As a result, either of the inputs to a gate 370 will be high all the time resulting in a flip-flop 372 always being reset. This high will allow 'QAL' to pass through two gates 374 and 376 to toggle two shift registers 378 and 380. The 'IVS' input and 'DVS' (delayed video) are therefore shifted through at a '$\phi$AL' rate. The '$\overline{IVS}$' and 'DVS' signals and their corresponding shift register outputs are fed to five exclusive OR gates 383, 384, 386, 388 and 390. Anytime both inputs to these gates are simultaneously high or low their outputs will be low, which is the case when the signals do not compare and there is an error condition. Any time, when the inputs are opposite, (the data identical), the outputs are high. The C20 to C24 outputs then feed a majority gate counter 392, shown in FIG. 26. The table, as shown in FIG. 27 requires that 3 of the 5 inputs A1, A2, B1, B2, and C1 must be high to indicate a good comparison at the S4 output of the counter 392. 'COMP' is then synchronized with '$\phi$AL' at a flip-flop 394 to establish an error signal, as required. With a high 'COMP' signal, the Q output of the flip-flop 394 will go low. Had the inputs to the counter 392 not compared in at least three of the five inputs, the Q output of the flip-flop 394 would have gone high at '$\phi$AL'. The set input to the flip-flop 394 holds the Q output low at the times of system operation when we do not desire an error indication.

With the hex switch in the least sensitive position 'O' the common (MASK) input to the switch will be open causing all the FP inputs to seek the level of the input 10K resistors. In this case FP23 will be high and FP22 low. This results in the release of the reset of the flip-flop 372 and the generation $\phi$BL/2 at the Q output. Gates 374 and 376 provide a $\phi$AL/2 toggle to the shift registers 378 and 380. The result is that a less stringent comparison of an every other clock comparison of the video, at the exclusive or gates. Also at this time the B1 input to the counter 392 is held high resulting in a need to only compare the remaining four inputs to get a 2/4 ratio.

It should be noted that the B1 input to the counter 392 is held high for a 2/4 comparison and low for a more critical comparison of ¾. For example in the 'O' position of the hex switch FP20 is high and FP21 low. This results in a gate 396 always providing a high at B1. Now only two of the four remaining inputs (A1,2,B2, C) need compare to have a non-error condition. If now for example, the 'F' position is selected the FP20 input will be high causing the gate 396 to always provide a low to the B1 input. This now requires that at least three of the remaining four inputs must compare resulting in the more stringent comparison of 3/5. Any other switch position that FP20 and FP21 are both held low will allow the C22 input to switch position that FP20 and FP21 are both held low will allow the C22 input to pass to the B1 input and allowing for a ¾ comparison of the plate pattern mask (clear) area.

As can be seen in FIG. 27 there is one condition where the output of 392 is incorrect. At the time of A,B,$\overline{A2},\overline{B2}$,C1 there is an 'O' output at S4 for a comparison of 3 out of 5 inputs, that is corrected with a gate 398.

As can be seen at the hex chart of FIG. 14 there is also the option of comparison the video for every clock pulse (1) in the opaque area and the translucent area every other clock (½), or the inverse of comparing the opaque area every other clock and the translucent area every other clock. The optimum setting is yet to be determined, but the hex 5 position is probably the most desirable since it provides a more stringent test of the clear areas and a less stringent one in the dark areas. The slit areas are more likely to have an acceptable variation such as a slight waviness, or unevenness that in a manufacturing environment would be an annoyance to consider an error.

We claim:

1. An inspection system for detecting defects in regular patterns wherein the elements of the patterns have variations in spatial period, said system comprising
   means for scanning and detecting the elements of a pattern,
   means for processing an output signal from said means for scanning and detecting during scanning, said means for processing including means for quantizing the output signal from the scanning and detecting means into binary digital signals, main storage means for storing the quantized signal of a portion of a scan, means for determining element period from the quantized signal and for controlling the output of said main storage means at times related to element period, means for correlating the output from said main storing means with a real time quantized signal of the same scan, and means for indicating the presence of an error related to a pattern defect in response to a miscorrelation signal from said correlating means.

2. The inspection system as defined in claim 1 wherein said processing means includes second storage means at the output of said quantizing means for storing a complete quantized scan signal.

3. The inspection system as defined in claim 2 wherein said processing means includes means, which include said second storage means, for gating out incomplete quantized signals to prevent their storage in said main storage means.

4. The inspection system as defined in claim 2 wherein said processing means includes means, which include said second storage means, for indicating alignment of the scanning and detecting means with a pattern.

5. The inspection system as defined in claim 1 wherein said processing means includes means for determining pattern type.

6. The inspection system as defined in claim 1 wherein said processing means includes means for visually displaying the spacing between pattern elements.

7. The inspection system as defined in claim 1 wherein said processing means includes a leading edge detector located between the output of said main storage means and an input of said means for determining and controlling for detecting the transition from a clear area to an element of a pattern.

8. The inspection system as defined in claim 1 wherein said processing means includes means for manually adjusting the sensitivity of the correlating means.

9. The inspection system as defined in claim 1 wherein said processing means includes another storage means for storing a miscorrelation signal from the correlating means for a scan and means for comparing the stored miscorrelation signal with an output of the correlating means for a subsequent scan.

10. An inspection system for detecting defects in regular patterns wherein the elements of the patterns have variations in spatial period, said system comprising a video sensor positioned to receive light from a regular pattern, means for scanning the video sensor over the regular pattern, means for processing an output signal from the video sensor during scanning, said means for processing including means for quantizing the output signal from the video sensor into binary digital signals, a variable length shift register for storing the quantized signal of a portion of a scan, means for determining element period from the quantized signal and for controlling the output of said variable length shift register at times related to element period, means for correlating the output from variable length shift register with a real time quantized signal of the same scan, and means for indicating the presence of an error related to a pattern defect in response to a miscorrelation signal from said correlating means.

* * * * *